US011648255B2

(12) United States Patent
Mraz et al.

(10) Patent No.: US 11,648,255 B2
(45) Date of Patent: May 16, 2023

(54) INHIBITORS FOR TREATMENT OF HEMATOLOGICAL MALIGNANCIES

(71) Applicants: Masarykova Univerzita, Brno (CZ); Fakultni Nemocnice Brno, Brno (CZ)

(72) Inventors: Marek Mraz, Brno (CZ); Vaclav Seda, Moravsky Krumlov (CZ); Laura Ondrisova, Bratislava (SK)

(73) Assignees: MASARYKOVA UNIVERZITA, Brno (CZ); FAKULTNI NEMOCNICE BRNO, Brno (CZ)

( * ) Notice: Subject to any disclaimer, the term of this patent is extended or adjusted under 35 U.S.C. 154(b) by 64 days.

(21) Appl. No.: 16/920,831

(22) Filed: Jul. 6, 2020

(65) Prior Publication Data
US 2022/0000879 A1  Jan. 6, 2022

(51) Int. Cl.
| A61K 31/5377 | (2006.01) |
|---|---|
| A61K 31/381 | (2006.01) |
| A61K 31/4164 | (2006.01) |
| A61K 31/496 | (2006.01) |
| A61K 31/4196 | (2006.01) |
| A61K 31/519 | (2006.01) |
| A61K 31/4245 | (2006.01) |
| A61K 31/196 | (2006.01) |
| A61K 31/433 | (2006.01) |
| A61K 31/4436 | (2006.01) |
| A61K 45/06 | (2006.01) |
| A61P 35/00 | (2006.01) |
| A61P 35/02 | (2006.01) |

(52) U.S. Cl.
CPC ........ *A61K 31/5377* (2013.01); *A61K 31/196* (2013.01); *A61K 31/381* (2013.01); *A61K 31/4164* (2013.01); *A61K 31/4196* (2013.01); *A61K 31/4245* (2013.01); *A61K 31/433* (2013.01); *A61K 31/4436* (2013.01); *A61K 31/496* (2013.01); *A61K 31/519* (2013.01); *A61P 35/00* (2018.01); *A61P 35/02* (2018.01); *A61K 45/06* (2013.01)

(58) Field of Classification Search
CPC ............... A61K 31/196; A61K 31/381; A61K 31/4164; A61K 31/4196; A61K 31/4245; A61K 31/427; A61K 31/433; A61K 31/44; A61K 31/4436; A61K 31/496; A61K 31/506; A61K 31/519; A61K 31/5377; A61K 31/63; A61K 45/06; A61P 35/00; A61P 35/02
See application file for complete search history.

(56) References Cited

U.S. PATENT DOCUMENTS

| 2002/0115112 A1* | 8/2002 | Yu ..................... C07K 14/70575 |
|---|---|---|
| | | 435/7.2 |
| 2014/0377258 A1* | 12/2014 | Stern ....................... A61K 45/06 |
| | | 514/263.22 |

FOREIGN PATENT DOCUMENTS

| WO | WO-2008064018 A1 * | 5/2008 | ........... C07D 519/00 |
| WO | WO-2016054642 A1 * | 4/2016 | ............. A01N 41/10 |
| WO | WO-2018089890 A1 * | 5/2018 | ........... A61K 31/475 |

OTHER PUBLICATIONS

Bertacchini et. al., Cell. Mol. Life Sci., publ. 2015, vol. 72, pp. 2337-2347 (Year: 2015).*
Noureldine et. al., Curr. Opin. Oncol., publ. 2015, vol. 27, pp. 21-25 (Year: 2015).*
Seda et. al., Eur. J. Haematol., publ. 2014, vol. 94, pp. 193-205 (Year: 2014).*

* cited by examiner

*Primary Examiner* — Sarah Pihonak
(74) *Attorney, Agent, or Firm* — Notaro, Michalos & Zaccaria P.C.

(57) ABSTRACT

A new approach to treatment of hematological malignancies. A GAB1 inhibitor for use in a method of treatment of a hematological malignancy is disclosed. The GAB1 inhibitor may be administered alone, or simultaneously or sequentially with a BTK inhibitor to achieve a synergistic effect.

114 Claims, 7 Drawing Sheets
Specification includes a Sequence Listing.

INHIBITORS FOR TREATMENT OF HEMATOLOGICAL MALIGNANCIES

FIELD AND BACKGROUND OF THE INVENTION

Field of the Invention

The present invention relates to treatment of hematological malignancies.

Background

Hematological malignancies represent a diverse group of diseases, including mostly myeloproliferative neoplasms, myelodysplastic syndromes, acute myeloid leukemia, mature B cell neoplasms, mature T cell and NK cell neoplasms or Hodgkin's lymphomas and myelomas. The Leukemia and Lymphoma society estimates that approximately 10% of new cancer diagnosis are hematological malignancies. While medical advance has improved cancer survival rates, there is a continuing need for new and more effective treatment.

Hematological malignancies are characterized by dysregulated cell proliferation and accumulation of malignant clones in peripheral blood and/or lymphoid tissues such as the spleen, bone marrow, or lymph nodes. This uncontrolled proliferation usually occurs in the microenvironment of lymph organs, where the malignant cells are provided with a variety of supportive stimuli that may contribute to drug resistance and the presence of residual disease after therapy. This was well illustrated in chronic lymphocytic leukemia (CLL) cells which are highly dependent on constant re-circulation between peripheral blood and lymphatic niches where they obtain pro-proliferative and anti-apoptotic signals. These pro-survival and pro-proliferative signals within microenvironment of lymphoid and myeloid malignancies typically include activation of PI3K/AKT axis. The migration of malignant myeloid cells, as well as the re-entry of malignant lymphoid cells to the microenvironment, is known to be guided by chemokine receptors such as CXCR4 (C-X-C chemokine receptor type 4) and CCR7 (C-C chemokine receptor type 7) and their ligands such as SDF1 (Stromal cell-derived factor 1) [Seda et Mraz, Eur J Haematol. 2015 March; 94(3):193-205; Voermans et al., Leukemia. 2002 April; 16(4):650-7.]. However, it still remains largely unclear how malignant cells precisely regulate their migration to immune niches or their survival outside of immune niches.

We and others have previously shown that GAB1 (GRB2-associated-binding protein 1) has a crucial role in the docking of various proteins to the cell membrane that allows transmission of the pro-survival signal to PT3K/AKT downstream. The activation of PT3K/AKT plays an important role in the pathophysiology of many hematological malignancies of both myeloid [Sophie Park et al., Haematologica. 2010 May; 95(5): 819-828] and lymphoid origin [Seda et Mraz, Eur J Haematol. 2015 March; 94(3):193-205]. This was well illustrated in B cells which are strongly dependent on so called "tonic" signaling that maintains their basal PI3K/AKT activity or activation of PI3K/AKT by cell-cell interactions or BCR engagement. However, the molecular pathway(s) regulating the activity of PI3K/AKT signaling are mostly poorly understood.

Moreover, it has been reported that multiple therapeutic strategies such as inhibition of BTK kinase or FLT3 or other kinases or use of chemo- or radiation-therapy leads to compensatory activation of other pro-survival signaling pathways in neoplastic cells, which might include the PI3K/AKT pathway.

DETAILED DESCRIPTION OF THE INVENTION

Figure 1A:
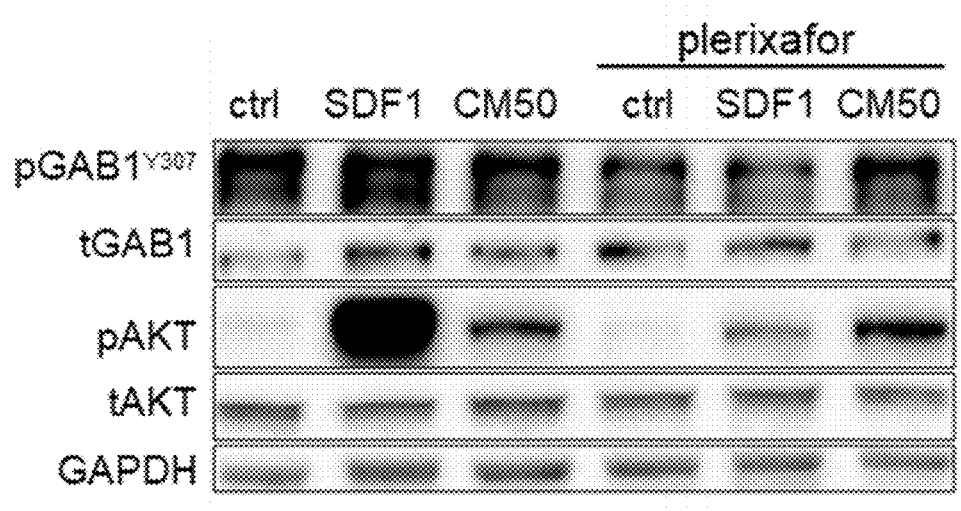
FIG. 1A shows a result from the stimulation of primary CLL cells by SDF1 or by conditioned media obtained from HS5 stroma cells.

The present invention provides a method of treatment of at least one hematological malignancy, in particular lymphoid or myeloid malignancy, said method comprising the step of administering at least one GAB1 inhibitor to a subject in need of such treatment. Within the framework of the present invention, it was shown that inhibition of GAB1 in malignant lymphocytes inhibits their migration, tonic signaling and key pro-survival pathways. Within the framework of the present invention, it was shown that inhibition of GAB1 induces cell death in malignant lymphoid and malignant myeloid cells.

In an aspect, the present invention provides a GAB1 inhibitor for use in the treatment of hematological malignancies, in particular lymphoid malignancies or myeloid malignancies.

The GAB1 protein is a member of the IRS1-like docking protein family. So far, the targeted approaches to treatment of hematological malignancies are based on inhibition of various kinases. The present invention is a novel therapy of hematological malignancies based on targeting a docking protein.

In an aspect of the invention, a method of treatment of at least one hematological malignancy, in particular lymphoid malignancy or myeloid malignancy is provided, said method comprising the step of co-administering at least one GAB1 inhibitor and at least one BTK inhibitor. Within the framework of the present invention, it was found that BTK inhibitors lead to the compensatory activation of PI3K-AKT pathway in malignant cells via GAB1 pathway induction, and therefore the GAB1 inhibition decreases or prevents the compensatory activation of AKT. Simultaneous inhibition of GAB1 and BTK are synergistic.

"Co-administering" or "co-administration" includes simultaneous administration and sequential administration. When administered simultaneously, the active ingredients (inhibitors) may be administered in one dosage form or in separate dosage forms. When administered sequentially, the active ingredients (inhibitors) may be administered in separate dosage forms, or in a single dosage form from which one active ingredient is released immediately and the other active ingredient is released in a controlled or sustained manner, or each active ingredient can be released in a controlled or sustained manner, wherein the controlled or sustained release profiles differ for each active ingredient. A single composition comprising at least two active ingredients (inhibitors) of the invention may be configured to release the active ingredients simultaneously, sequentially, immediately, or in a controlled or sustained manner. Excipients and auxiliary substances for various dosage forms and various forms of release are known to a person skilled in the art of pharmaceutical formulation.

In an aspect of the invention, a method of treatment of at least one hematological malignancy, in particular lymphoid malignancy or myeloid malignancy is provided, said method comprising the step of sequentially administering at least one GAB1 inhibitor and at least one BTK inhibitor.

In an aspect of the invention, a method of treatment of at least one hematological malignancy, in particular lymphoid malignancy or myeloid malignancy is provided, said method comprising the step of simultaneously administering at least one GAB1 inhibitor and at least one BTK inhibitor.

In an aspect, the invention provides a combination of a GAB1 inhibitor and a BTK inhibitor for use in the treatment of hematological malignancies, in particular lymphoid malignancies or myeloid malignancies.

In an aspect, the present invention provides a method of treatment of at least one hematological malignancy, in particular lymphoid malignancy or myeloid malignancy, said method comprising the step of administering at least one GAB1 inhibitor wherein the treatment of hematological malignancies, in particular lymphoid malignancies or myeloid malignancies, proceeds in particular via inhibiting the malignant cell migration, tonic signaling, antigen-induced signaling, and/or inducing the cell death.

In an aspect, the present invention provides a method of treatment of at least one hematological malignancy, in particular lymphoid malignancy or myeloid malignancy, said method comprising the step of co-administering at least one GAB1 inhibitor and at least one BTK inhibitor, wherein the treatment of hematological malignancies, in particular lymphoid malignancies or myeloid malignancies, proceeds in particular via inhibiting the activation of AKT pathway, inhibiting the malignant cell migration, tonic signaling, antigen-induced signaling, and/or inducing the cell death.

Terms used herein shall be accorded the following defined meanings unless otherwise indicated.

As used herein, the term "GAB1" refers to Grb2-associated protein 1 (Uniprot ID: Q13480). Preferably, GAB1 is a human GAB1.

As used herein, the term "BTK" refers to Bruton's tyrosine kinase (Uniprot ID: Q06187). Preferably, BTK is a human BTK.

The term "GAB1 inhibitor" or "inhibitor of GAB1" is used to signify a compound which is capable of interacting with a GAB1 and inhibiting its activity, or able to downmodulate GAB1 levels. Inhibiting GAB1 activity means reducing the ability of GAB1 to be phosphorylated (in particular at tyrosine 307 or tyrosine 627), or to interact with other proteins or with molecules in the cytoplasmic membrane. The term "BTK inhibitor" or "inhibitor of BTK" is used to signify a compound which is capable of interacting with a BTK and inhibiting its activity. Inhibiting BTK activity means reducing the ability of BTK to be phosphorylated, or to phosphorylate other proteins, or to interact with other proteins or molecules in cytoplasmic membrane or cytoplasm.

The term "an inhibitor" or "the inhibitor" should be interpreted as meaning one or more inhibitors of the specified target.

The term "B cell receptor" or "BCR" is used to signify a membrane protein complex that is widely expressed in B cells and it consists of surface immunoglobulin, which is usually coupled with CD79 proteins.

The term "B cell receptor activation" or "BCR activation" or "antigen-induced" is used to signify the process which occurs in the presence of antigen/ligand, which leads to activation of BCR. This could be measured by crosslinking of BCR complexes and phosphorylation of downstream kinases like CD79 (Cluster of differentiation 79), LYN (LYN proto-oncogene, Src family tyrosine kinase) or SYK (Spleen associated tyrosine kinase).

The term "induced signaling" is used to signify the process which occurs in the presence of antigen/ligand and leads to stronger phosphorylation of at least one downstream kinase in comparison to non-stimulated control cells. An assessment of induced signaling can be made by measurement of CD79, SYK, LYN, ZAP70, FLT3, ERK or AKT phosphorylation by immunoblot after exposure to an agent/antigen/ligand. Term "non-stimulated cells" means the condition of an environment where no external agent/antigen/ligand is present.

The term "tonic signaling" is used to signify a process of basal lymphoid or myeloid cell activation, which is based on PIK3/AKT activation in non-stimulated cells. Term "non-stimulated cells" means the condition of an environment where no external antigen/ligand is present.

The term "downregulation" is used to signify any process which leads to a reduction of protein or mRNA levels in affected cells in comparison to non-affected cells.

The term "upregulation" is used to signify any process, which leads to increasing of protein or mRNA levels in affected cells in comparison to non-affected cells.

The phrase "inhibition of cell migration" is used to denote the ability of a compound to inhibit malignant cell migration as compared to cells not contacted with the mentioned inhibitors. An assessment of cell migration can be made by transwell assay using malignant cells, agents inhibiting GAB1, or BTK activity or its mRNA or protein levels, chemo-attractants (like SDF1) and transwell. Such an assessment of cell migration can be made by measuring the number of migrated cells.

The phrase "inhibition of tonic signaling" is used to denote the ability of a compound to inhibit tonic signaling in malignant cells as compared to non-treated cells. An assessment of tonic signaling can be made by the measurement of basal AKT phosphorylation by immunoblot of flow cytometry. The term "basal AKT activity" is used to denote the basal phosphorylation of AKT at serine 473.

The phrase "inhibition of induced signaling" is used to denote the ability of a compound to inhibit induced signaling in malignant cells as compared to non-treated cells. An assessment of induced signaling can be made by measurement of SYK, LYN, ZAP70, FLT3, ERK or AKT phosphorylation by immunoblot after exposure to an agent/antigen/ligand.

The term "patient" or "subject in need of treatment", as used herein, means an animal, preferably a mammal, more preferably a human, suffering from a hematological malignancy. In some embodiments, the patient is a patient at diagnosis, or at risk of developing or experiencing a recurrence of hematological malignancy, or resistance to BTK inhibitor.

The expression "administering" or "administration" refers to administration of a therapeutically effective amount of an active ingredient.

The expression "therapeutically effective amount" refers to an amount of a drug substance (i.e., BTK, GAB1 inhibitors) effective for treatment of the disease or slowing down the progress of the disease or prevention of recurrence of a hematological malignancy discussed herein.

The expression "simultaneous administration" refers to the administration of two or more active ingredients substantially at the same time, wherein the active ingredients are present in one dosage form, or in two or more separate dosage forms.

The expression "sequential administration" refers to the administration of two or more active ingredients, each of them at a different point in time. I.e., one active ingredient is administered prior to, or after administration of another active ingredient. The time span between the administration is preferably at least 5 minutes, more preferably at least 30 minutes, or at least 1 hour, or at least 2 hours, or at least 3 hours.

The expressions "active ingredient", "drug substance", "active substance" are used herein as synonyms.

The hematological malignancies herein include malignancies associated with cells in the bloodstream, bone marrow, and the lymphoid system including in the liver, spleen, and lymph nodes. In particular, hematological malignancies include B-cell malignancies, T-cell malignancies, NK-cell malignancies, and myeloid malignancies i.e., B and T cell lymphomas and leukemias and myeloid leukemias. Examples of lymphomas include low grade/follicular lymphoma, small lymphocytic lymphoma (SLL), diffuse large B cell lymphoma, mantle cell lymphoma, marginal zone lymphomas, B or T cell lymphoblastic lymphoma, Burkitt's lymphoma, primary thyroid lymphoma, peripheral T cell lymphomas, NK cell lymphoma, Hodgkin's lymphoma, Waldenstrom's macroglobulinemia. Examples of leukemia include chronic lymphocytic leukemia (CLL), chronic myeloid leukemia (CML), lymphoblastic leukemia, myeloid leukemia, acute myeloid leukemia (AML), acute lymphoblastic leukemia (ALL), T or B prolymphocytic leukemia, promyelocytic leukemia and monocytic leukemia. Further examples of hematological malignancies include multiple myeloma, myelodysplastic syndromes (MDS), myeloproliferative syndromes, myeloma. It should be known to those of skill in the art that these pathological conditions may also appear under different names due to differing/changing classification systems.

Preferably, the hematological malignancies are selected from low grade/follicular non-Hodgkin's lymphoma (NHL), small lymphocytic leukemia (SLL), diffuse large B cell lymphoma (DLBCL), mantle cell lymphoma, Burkitt's lymphoma, acute myeloid leukemia (AML), acute lymphoblastic leukemia (ALL), chronic lymphocytic leukemia (CLL).

The GAB1 and BTK inhibitors for use according to the present invention may be formulated in pharmaceutical dosage forms. The dosage forms may be formulated as a unit dosage form for ease of administration and uniformity of dosage. The expression "unit dosage" form, as used herein, refers to a physically discrete unit of agent appropriate for the patient to be treated. It will be understood, however, that the total daily usage of the compounds and compositions of the present invention to be decided by the attending physician within the scope of sound medical judgment. For example, a unit dosage form for parenteral administration may be in ampules or in multi-dose containers. A unit dosage form for oral administration may be a tablet, a capsule. Other dosage forms may include, for example, syrups, solutions, dispersions. The dosage forms contain, in addition to the active substance(s), pharmaceutically acceptable excipients such as fillers, binders, disintegrants, flavors, glidants, lubricants, preservatives, which are known to those skilled in the art of pharmaceutical formulation.

In the case of combination treatment, the GAB1 inhibitor may be administered with the BTK inhibitor in a single dosage form, or the inhibitors may be administered in separate dosage forms. When administered as a separate dosage form, the BTK inhibitor may be administered prior to, simultaneously, or after the administration of the GAB1 inhibitor.

The GAB1 inhibitor may, in some embodiments, be selected from the compounds shown in patent WO 2016/054642 A1 as GAB1 inhibitors. WO 2016/054642 and the compounds shown therein are hereby incorporated by reference.

In an aspect of the invention, the GAB1 inhibitor may be a compound of formula I:

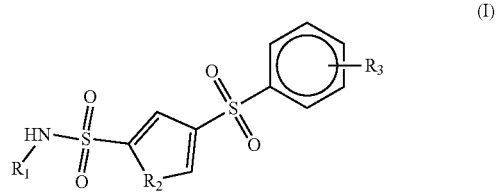

(I)

wherein
R2 is an S;
R3 is H, an alkyl, or a halogen; and

R1 is an aromatic heterocycle or formula II

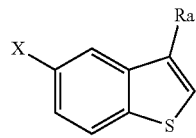

wherein R8 is an alkyl bonded to the NH group in formula I, and X is a halogen.

In an aspect of the invention, the GAB1 inhibitor may be a compound of formula III:

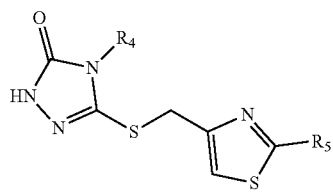

wherein

R5 is a benzene, or a (substituted) aryl group, or a (substituted) heteroaryl group; and R4 is a moiety of formula IV:

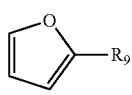

wherein R9 is an alkyl bonded to the N group in formula III.

In an aspect of the invention, the GAB1 inhibitor may be a compound of formula V:

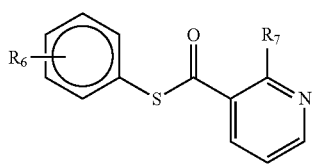

wherein

R6 is an H, an alkyl, or a halogen, R7 is a moiety of formula VI:

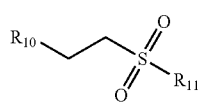

wherein R10 is an S or an alkyl bonded to the N-containing aromatic group of formula V; and R11 is an H or an alkyl.

The term "alkyl" refers to a saturated aliphatic chain, linear or branched, having 1-25 carbons, preferably 1-10 carbons, more preferably 1-6 carbons. Examples of alkyl are methyl, ethyl, propyl, isopropyl, butyl, isobutyl, tert-butyl, pentyl, hexyl, isohexyl, heptyl, 4,4-dimethylpentyl, octyl, 2,2,4-trimethylpentyl, nonyl, or decyl.

The term "alkenyl" is used herein to mean a straight or branched chain radical of 2-10 carbon atoms, unless the chain length is otherwise limited, wherein there is at least one double bond between two of the carbon atoms in the chain, including, but not limited to, ethenyl, 1-propenyl, 2-propenyl, 2-methyl-1-propenyl, 1-butenyl, 2-burenyl, and the like. Preferably, the alkenyl chain is 2 to 20 carbon atoms in length, most preferably from 2 to 12 carbon atoms in length.

The term "alkynyl" is used herein to mean a straight or branched chain radical of 2-10 carbon atoms, unless the chain length is otherwise limited, wherein there is at least one triple bond between two of the carbon atoms in the chain, including, but not limited to, ethynyl, 1-propynyl, 2-propynyl, and the like.

Preferably, the alkynyl chain is 2 to 20 carbon atoms in length, most preferably from 2 to 12 carbon atoms in length.

In all instances herein where there is an alkenyl or alkynyl moiety as a substituent group, the unsaturated linkage, i.e., the vinyl or ethynyl linkage, is preferably not directly attached to a nitrogen, oxygen or sulfur moiety.

The term "halogen" refers to an atom selected from fluorine, chlorine, bromine, and iodine.

The term "aryl" refers to monocyclic or bicyclic aromatic groups containing from 6 to 12 carbons in the ring portion, preferably 6-10 carbons in the ring portion. Typical examples include phenyl, biphenyl, naphthyl or tetrahydronaphthyl.

The term "heterocycle" refers to a cyclic moiety having 5 to 14 ring atoms, wherein 1, 2, 3 or 4 of the ring atoms are independently selected from oxygen, nitrogen and sulfur heteroatoms.

The term "heterocycle" may refer to a "heteroaryl." The term "heteroaryl" refers to a cyclic aromatic moiety having 5 to 14 ring atoms, wherein 1, 2, 3 or 4 of the ring atoms are independently oxygen, nitrogen or sulfur heteroatoms. Examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl, phenoxazinyl, and tetrazolyl groups.

The term "heterocycle" may also refer to a "heterocycloalkyl." "Heterocycloalkyls" as used herein may refer to any saturated or partially unsaturated heterocycle. "Heterocycloalkyl" refers to a saturated or partially unsaturated ring system having 5 to 14 ring atoms selected from carbon atoms and 1, 2, 3, or 4 oxygen, nitrogen, or sulfur heteroatoms. Typical saturated examples include pyrrolidinyl, imidazolidinyl, pyrazolidinyl, tetrahydrofuranyl, tetrahydropyranyl, piperidyl, piperazinyl, quinuclidinyl, morpholinyl, and dioxacyclohexyl. Typical partially unsaturated examples include pyrrolinyl, imidazolinyl, pyrazolinyl, dihydropyridinyl, tetrahydropyridinyl, and dihydropyranyl. Either of these systems can be fused to a benzene ring. When a substituent is oxo (i.e., =O), then 2 hydrogens on the atom are replaced. When aromatic moieties are substituted by an oxo group, the aromatic ring is replaced by the corresponding partially unsaturated ring. For example, a pyridyl group substituted by oxo results in a pyridone.

The phrase "substituted" when not explicitly defined refers to a group or groups being optionally substituted with one or more substituents independently selected from the group consisting of hydroxy, nitro, trifluoromethyl, halogen, $C_{1-6}$ alkyl, $C_{1-6}$ haloalkyl, $C_{1-6}$ alkoxy, $C_{1-6}$ alkylenedioxy, $C_{1-6}$ aminoalkyl, $C_{1-4}$ hydroxyalkyl, $C_{2-4}$ alkenyl, $C_{2-4}$ alkynyl, $C_{6-10}$ aryl, phenoxy, benzyloxy, 5-10 membered heteroaryl, $C_{2-6}$ aminoalkoxy, amino, mono($C_{1-4}$)alkylamino, di($C_{1-4}$)alkylamino, $C_{2-6}$ alkylcarbonylamino, $C_{2-6}$ alkoxycarbonylamino, $C_{2-6}$ alkoxycarbonyl, $C_{2-6}$ alkoxycarbonylalkyl, carboxy, $C_{2-6}$ hydroxyalkoxy, ($C_{1-6}$)alkoxy($C_{2-6}$)alkoxy, mono($C_{1-4}$)alkylamino($C_{2-6}$)alkoxy, di($C_{1-4}$)alkylamino($C_{2-6}$)alkoxy $C_{2-10}$ mono(carboxyalkyl)amino, bis($C_{2-10}$ carboxyalkyl)amino, $C_{2-6}$ carboxyalkoxy, $C_{2-6}$ carboxyalkyl, carboxyalkylamino, guanidinoalkyl, hydroxyguanidinoalkyl, cyano, trifluoromethoxy, perfluoroethoxy, aminocarbonylamino, mono($C_{1-4}$)alkylaminocarbonylamino, di($C_{1-4}$)alkylaminocarbonylamino, N—($C_{1-4}$)alkyl-N-aminocarbonyl-amino, N—($C_{1-4}$)alkyl-N-mono($C_{1-4}$)alkyl aminocarbonyl-amino or N—($C_{1-4}$)alkyl-N-di($C_{1-4}$) alkylaminocarbonylamino.

The term "monoalkylamino" as employed herein refers to the group $NH_2$ wherein one hydrogen has been replaced by an alkyl group, as defined above. The term "dialkylamino" as employed herein refers to the group $NH_2$ wherein both hydrogens have been replaced by alkyl groups, independently selected from the alkyls as defined above. The term "aminoalkyl" as employed herein refers to any of the above alkyl groups wherein one or more hydrogens thereof are substituted by one or more amino ($NH_2$) moieties.

The term "hydroxyalkyl" as employed herein refers to any of the above alkyl groups wherein one or more hydrogens thereof are substituted by one or more hydroxyl moieties.

The term "carboxyalkyl" as employed herein refers to any of the above alkyl groups wherein one or more hydrogens thereof are substituted by one or more carboxylic acid moieties.

The term "carboxy" refers to carboxylic acid moiety —COOH, or to a moiety —COO—.

The term "haloalkyl" as employed herein refers to any of the above alkyl groups wherein one or more hydrogens thereof are substituted by one or more halo moieties. Typical examples include fluoromethyl, difluoromethyl, trifluoromethyl, trichloroethyl, trifluoroethyl, fluoropropyl, and bromobutyl.

The term "alkoxy" or "alkyloxy" refers to any of the above alkyl groups linked to an oxygen atom. Typical examples are methoxy, ethoxy, isopropyloxy, sec-butyloxy, and t-butyloxy.

The term "heteroatom" is used herein to mean an oxygen atom ("O"), a sulfur atom ("S") or a nitrogen atom ("N"). It will be recognized that when the heteroatom is nitrogen, it may form an $NR_aR_b$ moiety, wherein $R_a$ and $R_b$ are, independently from one another, hydrogen or C1 to C8 alkyl, or together with the nitrogen to which they are bound form a saturated or unsaturated 5-, 6-, or 7-membered ring.

The terms "hydroxy" and "hydroxyl" are used interchangeably to refer to the radical —OH. The terms "pyridyl" and "pyridinyl" are used interchangeably to refer to a monovalent radical of pyridine.

The terms "carbamoyl" and "aminocarbonyl" are used interchangeably to refer to the radical $NH_2$—C(O).

The terms "ureido" and "aminocarbonylamino" are used interchangeably to refer to the radical $NH_2$—C(O)—NH—.

The term "alkoxycarbonyl" refers to the radical alkoxy-C(O)–.

In an aspect of the invention, the GAB1 inhibitor may be selected from:

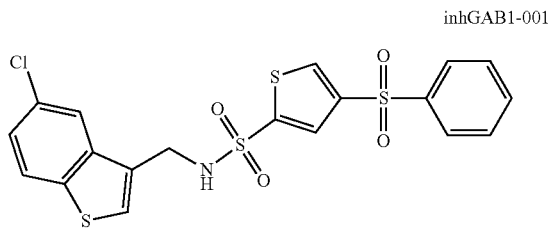

inhGAB1-001

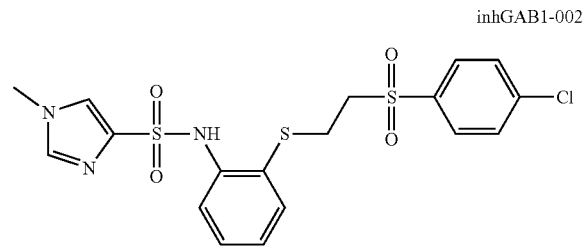

inhGAB1-002

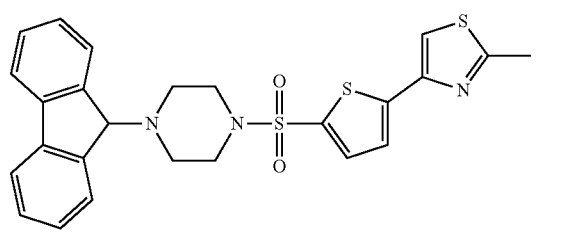

inhGAB1-003

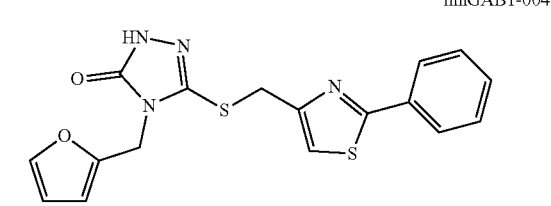

inhGAB1-004

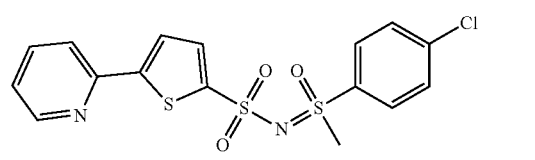

inhGAB1-005

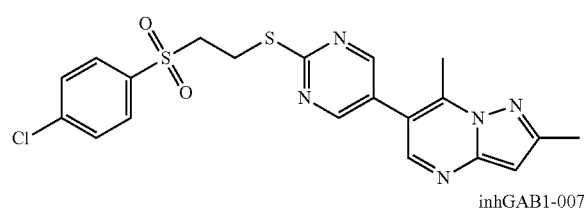

inhGAB1-006

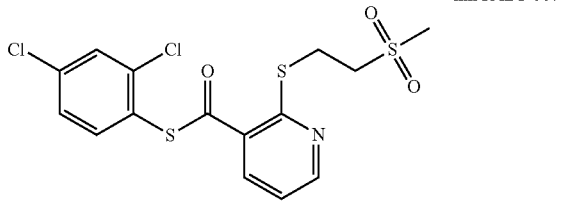

inhGAB1-007

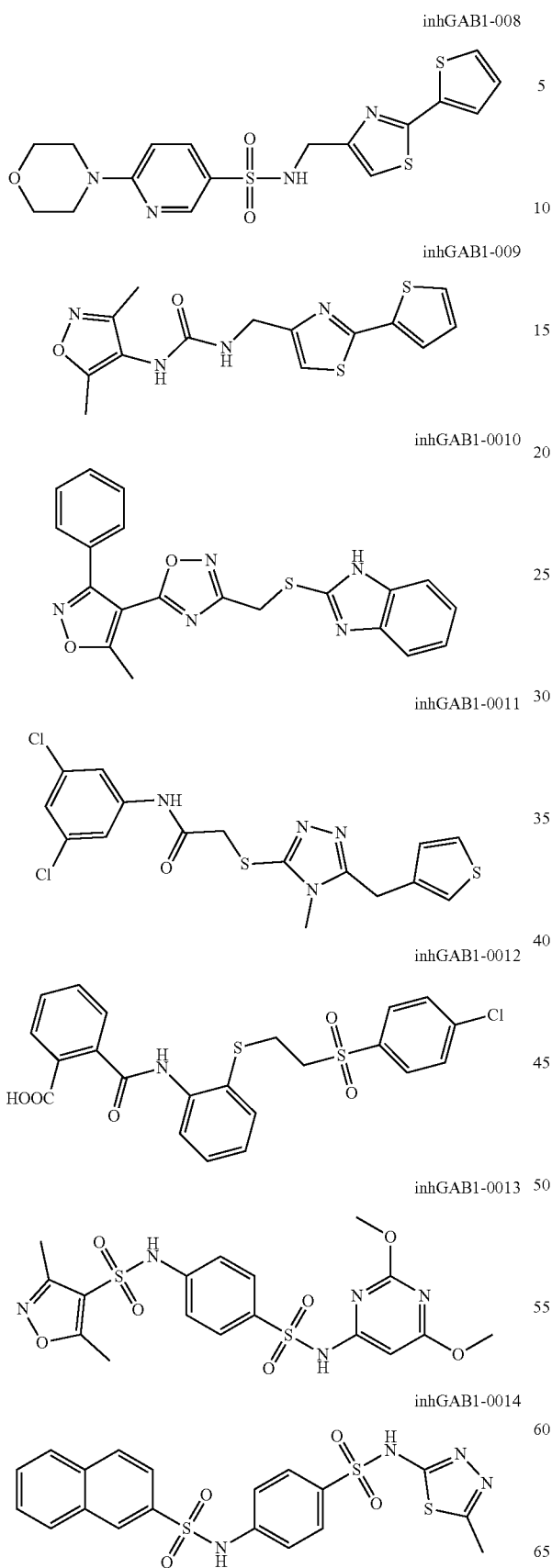
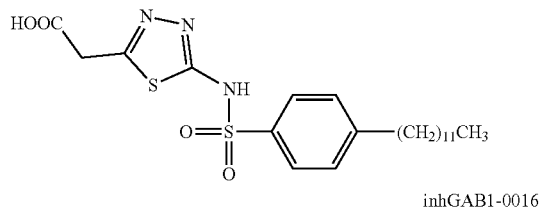
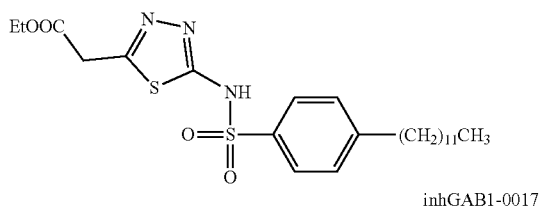
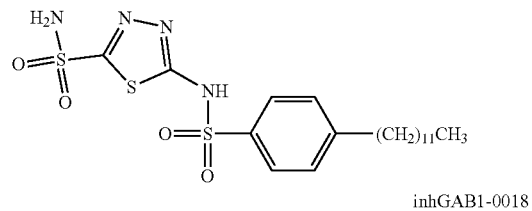
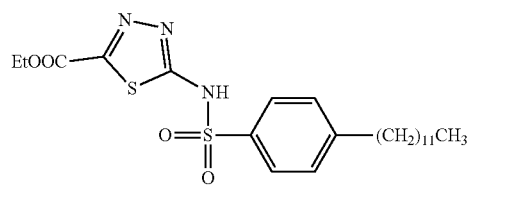
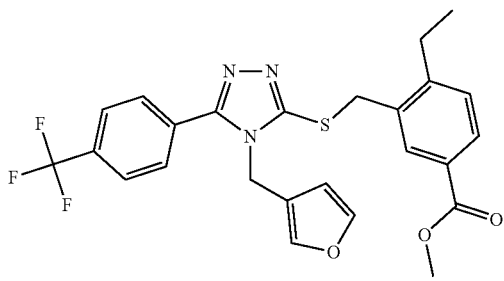
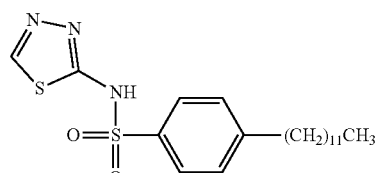
The BTK inhibitor may preferably be selected from ibrutinib, acalabrutinib, zanubrutinib, GDC-0834; RN-486; CGI-560; CGI-1764; HM-71224; CC-292; ONO-4059; CNX-774; and LFM-A13. They have the following structures:

PCI-32765
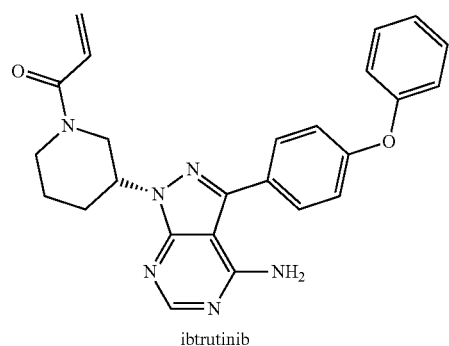
ibtrutinib
ACP-196
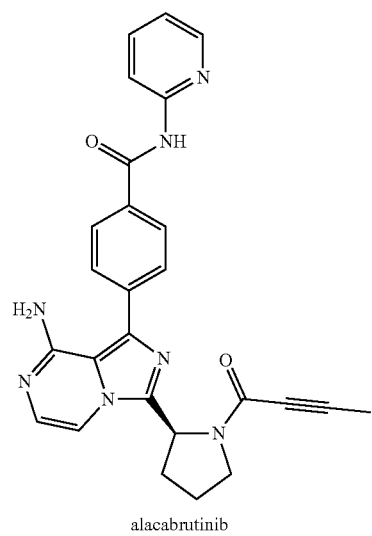
alacabrutinib
BGB-3111
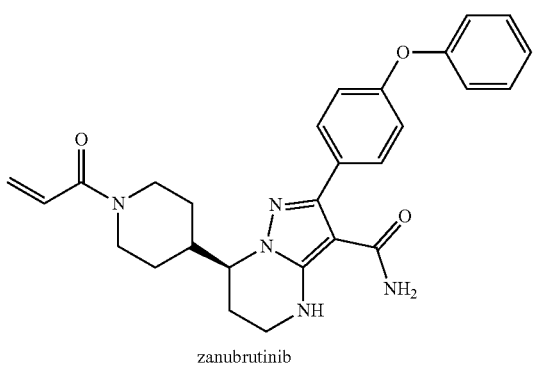
zanubrutinib
GDC-0834
RN486
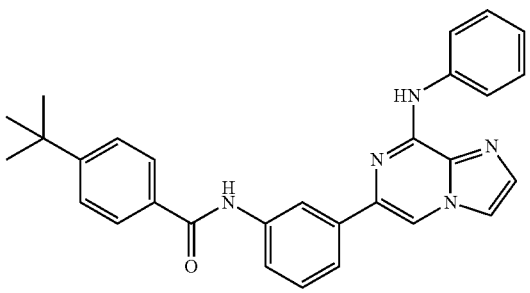
GCI-560
CGI-1764
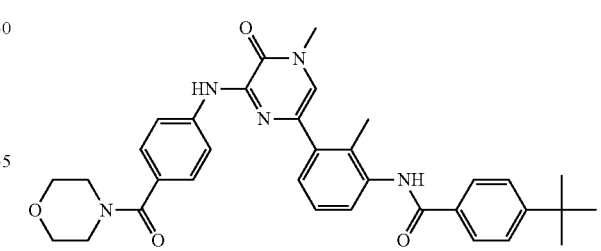
HM-71224
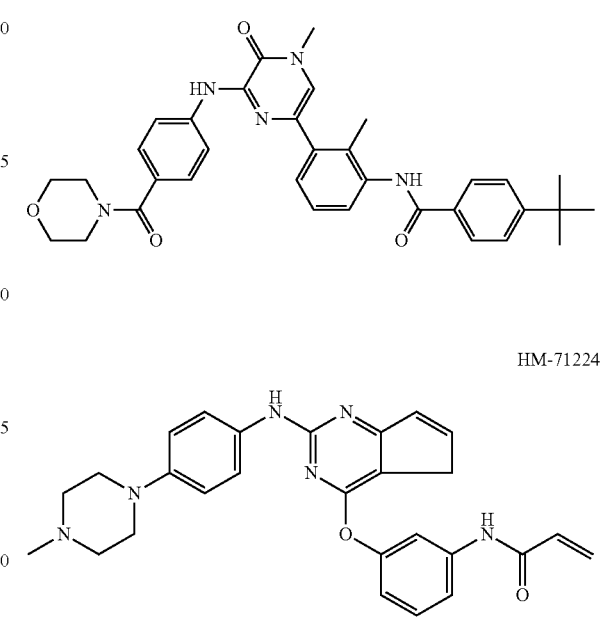
CC-292
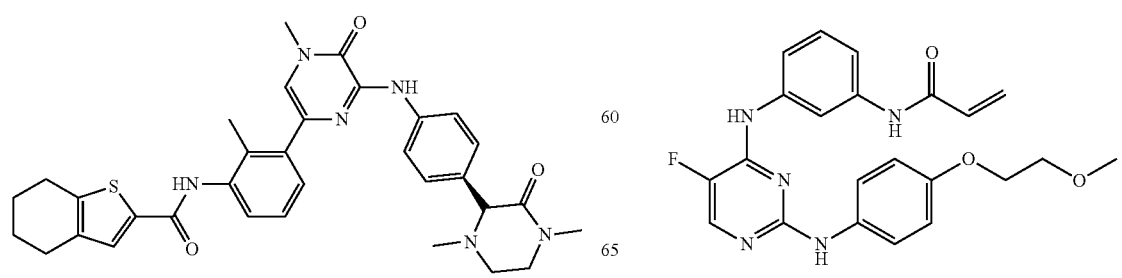

-continued

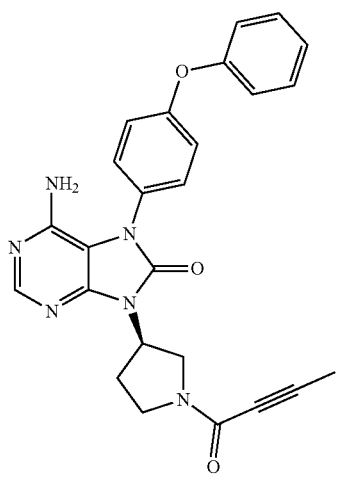

ONO-4059

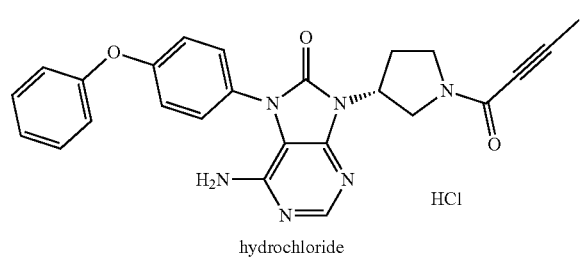

ONO-4059 hydrochloride

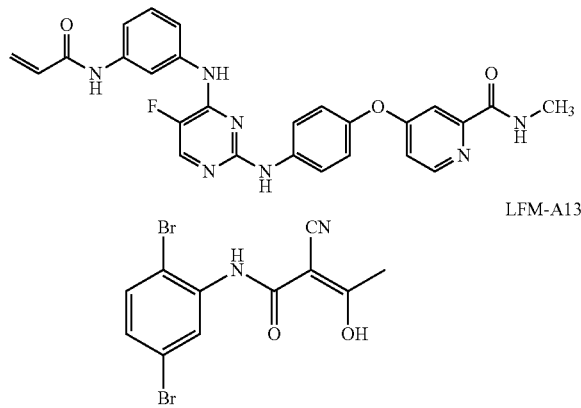

CNX-774

LFM-A13

EXAMPLES OF CARRYING OUT THE INVENTION

Materials and Methods

Cell Culture

Primary CLL samples were collected with written informed consent, and the Institutional Review Board approved the study. Peripheral blood samples were obtained from patients who did not receive any therapy for at least six months (except the ibrutinib-treated patients). The samples from ibrutinib-treated patients were collected at a day before ibrutinib administration and during therapy at the timepoints specifically mentioned in examples. All primary CLL samples were purified by negative selection with RosetteSep Human B Cell Enrichment Cocktail (catalog number: #15064; Stemcell Technologies) and RosetteSep Human CD3 Depletion Cocktail (catalog number: #15661; Stemcell Technologies) and Ficoll-Paque™ PLUS (catalog number: GE17-1440-02; Sigma Aldrich) according to manufacturer's protocol. Purified primary CLL cells were cultivated in RPMI-1640 (catalog number: R8758, Sigma-Aldrich) supplemented with 10% fetal bovine serum (catalog number: FB-1350; Biosera) and 5% penicillin/streptomycin (catalog number: P4333; Sigma Aldrich) and in 5% $CO_2$ at 37° C.

MEC1 cell line was obtained from the German Collection of Microorganisms and was cultivated in Iscove's Modified Dulbecco's Medium (IMDM, catalog number: 13390, Sigma-Aldrich) supplemented with 10% fetal bovine serum (catalog number: FB-1350; Biosera) and 5% penicillin/streptomycin (catalog number: P4333; Sigma Aldrich) and further cultivated in 5% $CO_2$ at 37° C.

OSU-CLL cell line was a kind gift from Dr. Byrd (The Ohio State University) and was cultivated in RPMI-1640 media (catalog number: R8758, Sigma-Aldrich) supplemented with 10% fetal bovine serum (catalog number: FB-1350; Biosera) and 5% penicillin/streptomycin (catalog number: P4333; Sigma Aldrich) and further cultivated in 5% $CO_2$ at 37° C.

RAMOS, DOHH2, GRANTA, WSU-NHL, JEKO, ML2 and OciLy5 cell lines were obtained from the German Collection of Microorganisms and were cultivated in RPMI-1640 (catalog number: R8758, Sigma-Aldrich) supplemented with 10% fetal bovine serum (catalog number: FB-1350; Biosera) and 5% penicillin/streptomycin (catalog number: P4333; Sigma Aldrich) and in 5% CO2 at 37° C.

HS5 cell line as well as HEK293-FT cell line were obtained from the German Collection of Microorganisms and both were cultivated in Dulbecco's Modified Eagle's Medium (DMEM, catalog number: D6429, Sigma-Aldrich) supplemented with 10% fetal bovine serum (catalog number: FB-1350; Biosera) and 5% penicillin/streptomycin (catalog number: P4333; Sigma Aldrich) and further cultivated in 5% $CO_2$ at 37° C.

Immunoblotting

The $5-20\times10^6$ of cells was lysed in 100 µl of lysis buffer (1% SDS, 50 mM TRIS-HC pH 6.8, 10% glycerol; all reagents were obtained from Sigma Aldrich, catalog numbers: L3771, T6066, H1758, G5516) with phosphatase and protease inhibitors (catalog number: P8340 and P0044; Sigma Aldrich). Samples were sonicated 2×10 seconds, amplitude 60% (type: UP100H; Hielscher). Protein concentration was further determined using DC Protein Assay (catalog number: 000112; BioRad) according to manufacturer protocol. In the next step, samples were diluted with lysis buffer (containing protease and phosphatase inhibitors obtained from Sigma Aldrich, catalog number: P8340 and P0044) to a final concentration of 3.5 µg/µl. The loading buffer (0.02% bromophenol blue v/v, 1% β-mercaptoethanol v/v in MQ water; all reagents were obtained from Sigma Aldrich; catalog numbers: B8026, M3148) was added to all samples. All samples were denatured by incubation at 98° C. for 5 minutes. Subsequently, equal amounts of protein (30 µg per sample) were separated by SDS-PAGE. Separation gel: 390 mM TRIS (pH 8.8), 10% acrylamide, 350 µM SDS, 440 µM APS, 2 µl TEMED, plus MQ water to final volume 5 ml of solution. Stacking gel:—125 mM TRIS (pH 6.8), 0.5% acrylamide, 350 µM SDS, 440 µM APS, 2 µl TEMED, plus MQ water to final volume 2 ml (all reagents were obtained from Sigma Aldrich; catalog numbers: L3771, T6066, H1758, A3574, A3678, T9281). Electrophoresis was conducted using Biorad Miniprotean system (Biorad) according to manufacturer protocol (voltage: 60-110 V, electrophoresis buffer: 25 mM TRIS, 250 mM glycine, 1%

SDS, pH 8.2; all reagents were obtained from Sigma Aldrich; catalog numbers: L3771, T6066, H1758, G8898). Proteins were subsequently transferred to the PVDF membrane (0.45 μm pore size, Millipore) using Biorad Miniprotean system (Biorad) according to manufacturer protocol (blot buffer: 20% methanol, 192 mM glycine, 25 mM TRIS; all reagents were obtained from Sigma Aldrich; catalog numbers: 34860, T6066, H1758, G8898). Next, the membranes were blocked by 5% BSA (catalog number: PM-T1726, Biosera) in Wash buffer (150 mM NaCl, 20 mM TRIS (pH 7.4), 0.1% Tween 20; all reagents were obtained from Sigma Aldrich; catalog numbers: S7653, T6066, H1758, P9416) for 1 hour. After that the membranes were incubated overnight at 4° C. with primary antibodies (provider, target, catalog number, compatible secondary antibody and concentration are specified in table below and in examples). Next day were membranes 3 times washed for 10 minutes by Wash buffer and subsequently loaded into secondary horse-radish peroxidase (HRP)-conjugated anti-mouse (#7076, Cell Signaling) or anti-rabbit antibodies (#7074, Cell Signaling), depending on the origin of primary antibody. Secondary antibodies were diluted to final concentration 1:2000 in 5% BSA in wash buffer. Membranes were washed 3 times for 10 minutes by Wash buffer. Immunocomplexes were detected by ECL Substrate (catalog number: 1705061; BioRad), which was used according to the manufacturer's protocol. Chemiluminescent signal was digitally detected with UVItec Alliance 4.7 (UVItec, Cambridge).

of Shapiro-Wilk test of normality of input data. Statistical analyses were performed with GraphPad Prism Software v5.0 (GraphPad Software). P-values≤0.05 were considered significant.

Example 1—GAB1 Increases the Malignant B Cell Migration Propensity, and GAB1 Inhibition Decreases Migration of Malignant B Cells Primary CLL cells ($5 \times 10^6$/ml) were cultured as described in Material and Method section. Three milliliters of cell suspension were treated with plerixafor (5 μg/ml) for 8 hours and another three milliliters of cell suspension were simultaneously treated with an equal volume of vehicle (PBS; catalog number: 5493; Sigma Aldrich) also for 8 hours. After that, the cells from each variant were equally divided into three tubes and each variant was subsequently stimulated by adding SDF1 ligand to final concentration 100 ng/ml or by adding conditioned media to a final concentration of 50% or by adding equal amount of PBS (ctrl; control; catalog number: 5493; Sigma Aldrich). Cells were washed after 5 minutes with cold PBS (4° C., 1 ml; catalog number: 5493; Sigma Aldrich) and subsequently lysed for immunoblot. The preparation of conditioned media and immunoblot protocol are described in the Material and Method section. To develop specific proteins we used these primary antibodies (concentration, catalog number, provider and origin): phospho-GAB1 Y307 (1:2000; #3234, Cell Signaling; rabbit); total-GAB1 (1:2000; #3232, Cell Signaling; rabbit); phos-

| Target | Provider | Catalog number | Concentration | Origin |
| --- | --- | --- | --- | --- |
| Total GAB1 | Cell Signaling | #3232 | 1:2000 | rabbit |
| Phospho-GAB1 (Y627) | Cell Signaling | #3233 | 1:2000 | rabbit |
| Phospho-GAB1 (Y307) | Cell Signaling | #3234 | 1:2000 | rabbit |
| Total AKT | Cell Signaling | #2920 | 1:3000 | mouse |
| Phospho-AKT (Ser473) | Cell Signaling | #4060 | 1:2000 | rabbit |
| Total Btk | Cell Signaling | #8547 | 1:2000 | rabbit |
| Phospho-Btk (Tyr223) | Cell Signaling | #87457 | 1:1000 | rabbit |
| Total ERK | Cell Signaling | #4696 | 1:3000 | mouse |
| Phospho ERK (Thr202/Tyr204) | Cell Signaling | #4377 | 1:3000 | rabbit |
| B-actin | Cell Signaling | #4970 | 1:5000 | rabbit |
| GAPDH | Cell Signaling | #2118 | 1:4000 | rabbit |

Conditioned Media Preparation

HS5 cells ($3.5 \times 10^6$) were seeded in T75 cultivation flask (TPP) in 12 ml of Dulbecco's Modified Eagle's Medium media (DMEM, catalog number: D6429, Sigma-Aldrich). The next day was original media discarded, the cells attached to the bottom of the flask were washed once with 10 ml of PBS (catalog number: 5493; Sigma Aldrich). Subsequently, the 25 ml of RPMI-1640 (catalog number: R8758, Sigma-Aldrich) media was added to the attached HS5 cells. After 48 hours was this conditioned media collected, purified from cell-debris by 10 minutes centrifugation at 2000 RCF and subsequently diluted with fresh RPMI-1640 media (catalog number: R8758, Sigma-Aldrich) containing 10% FBS (catalog number: FB-1350; Biosera) and 5% penicillin/streptomycin (catalog number: P4333; Sigma Aldrich) to final concentration 50% conditioned media. This media was immediately used for experiments.

Statistical Analysis

Differences in expression levels between paired samples were compared using paired t-test or Wilcoxon matched matched-pairs test, and differences in non-matched groups were compared using unpaired t-test or Mann-Whitney U test. The appropriate tests were chosen based on the results pho-AKT Ser473 (1:2000; #4060, Cell Signaling; rabbit); total-AKT (1:3000; #2920, Cell Signaling; mouse); GAPDH (1:4000; #2118, Cell Signaling; rabbit). Secondary antibodies were antibodies conjugated with horse-radish peroxidase (HRP) showing specificity against primary antibodies produced in mouse (1:3000; #7076, Cell Signaling) or rabbit (1:2000; #7074, Cell Signaling). The selection of the secondary antibody was dependent on the origin of the primary antibody.

FIG. 1A shows a result from the stimulation of primary CLL cells by SDF1 or by conditioned media obtained from HS5 stroma cells. This revealed that treatment with SDF1 or soluble factors produced by HS5 cells (conditioned media, CM) leads to phosphorylation and thus activation of GAB1 protein. The treatment of cells with conditioned media in the presence of a specific CXCR4 inhibitor plerixafor also led to GAB1 phosphorylation, suggesting that activation of other chemokine-pathways or action of soluble factors other than SDF1 also includes GAB1 activation.

MEC1 cells ($2.5 \times 10^6$/ml) or primary CLL cells ($5 \times 10^6$/ml) were transfected in 100 μl reaction by NEON transfection system (catalog number: MPK10096; ThermoFisher Scientific) according to manufacturer protocol (program 1200 V/20 ms/2 pulses). The transfection buffer was supplemented with specific siRNA targeting GAB1 mRNA (ON-TARGETplus siRNA—Human; catalog number: L-003553-00-0005; Dharmacon) or nonspecific siRNA (ON-TARGETplus Non-targeting Pool; catalog number: D-001810-10-05; Dharmacon) to final concentration 1000 nM. Cells were incubated for 48 hours in IMDM media as described in the Material and Method section. After that, the competitive migration assay was executed by staining of transfected MEC1 cells with CFSE (Thermo Fisher Scientific, catalog number: C34554) or FarRed (Thermo Fisher Scientific, catalog number: C34564) CellTrace dye. Each transfection variant was stained separately with one of these dyes according to manufacturer protocol. Cells were incubated overnight. The next day, the stained control cells (transfected with nonspecific siRNA) and GAB1-attenuated cells (transfected with siRNA specific to GAB1 mRNA) were analyzed for viability (stained with Sytox Blue according to manufacturer protocol; Thermo Fisher Scientific, catalog number: S34857). Paired samples with low viability (<80%) were excluded from further experiments as well as samples where the difference in viability between paired samples was higher than 5%. To compare the migration, the stained cells were mixed in ratio 1:1 and loaded in transwell inserts (24-well insert, 8 μm pore size; Falcon, Corning) according to manufacturer protocol. The migration towards SDF1 (100 ng/ml, Peprotech, catalog number: 300-28A) or conditioned media (diluted to final concentration 50%; preparation of conditioned media is described in Material and Method section) was allowed for 6 hours and subsequently the ratio of migrated (cells migrated through the transwell) CFSE or FarRed positive cells was detected by flow cytometry (BD FACS Verse, BD Biosciences). To detect the signal by flow cytometry, we followed the instructions provided by the manufacturer of these dyes (Thermo Fisher Scientific). The percentage of control cells was set to 1. The ratio of migrated GAB1-attenuated cells to the control cells was calculated by dividing of the percentage of migrated GAB1-attenuated cells by percentage of migrated control cells Tab. 1A shows a result for the migration capacity of MEC1 cells after silencing of GAB1 by specific siRNA. The silencing of GAB1 largely inhibited the migration of MEC1 cells towards conditioned media in comparison to cells transfected with negative control (competitive migration assay).

Tab.1B shows a result for the migration capacity of primary CLL cells after the silencing of GAB1 by specific siRNA. The silencing of GAB1 largely inhibited the migration of primary CLL cells towards conditioned media in comparison to cells transfected with negative control (competitive migration assay).

TABLE 1A

| | Ratio of migrated cells | P value (sample compared to control) | SD (standard deviation) | N (number of replicates) |
|---|---|---|---|---|
| non-specific siRNA (control) | 1 | — | — | 3 |
| GAB1 specific siRNA | 0.52 | 0.03 | 0.13 | 3 |

TABLE 1B

| | Ratio of migrated cells | P value (sample compared to control) | SD (standard deviation) | N (number of replicates) |
|---|---|---|---|---|
| non-specific siRNA (control) | 1 | — | — | 3 |
| GAB1 specific siRNA | 0.74 | 0.02 | 0.057 | 3 |

To obtain the $MEC1^{GAB1-less}$ cell line, $MEC1^{wt}$ (wild-type) cells ($2.5 \times 10^6$/ml) were transfected by NEON transfection system (catalog number: MPK10096; Thermo Fisher Scientific) with 2 μg of pSpCas9(BB)-2A-GFP (PX458) (Addgene plasmid #48138) containing the gRNA targeting the second exon of GAB1 gene. This gRNA was designed in Benchling online tool and its sequence 5'-CTACTTGGTAGCAGACAGCG-3' (SEQ ID NO: 1) was cloned into pSpCas9(BB)-2A-GFP vector before transfection according to instructions published in (Genome engineering using the CRISPR-Cas9 system, Nature Protocols volume 8, pages 2281-2308(2013)). After 48 hours, the cells were sorted (BD FACS Aria Fusion, BD Biosciences) according to viability (stained with Sytox Blue according to manufacturer protocol; Thermo Fisher Scientific) and GFP-positivity. Sorted cells were cultured for two weeks (see Material and Method section). The expression of GAB1 protein was subsequently validated by immunoblot (see Material and Method section).

The competitive migration assay was performed as described in the previous section. Here, the control cells are named as $MEC1^{wt}$ and GAB1-less cells are named as $MEC1^{GAB1-less}$. Results for competitive migration assay were calculated as described in the previous section.

Tab. 1C shows result for the migration capacity of MEC1 cells after attenuation of GAB1 expression by CRISPR-Cas9 technology ($MEC1^{GAB1-less}$) in comparison to wild-type MEC1 cells (MEC1). The attenuation of GAB1 expression largely inhibited the migration of MEC1 cells towards conditioned media in comparison to wild type cells (competitive migration assay).

TABLE 1C

| | Ratio of migrated cells | P value (sample compared to control) | SD (standard deviation) | N (number of replicates) |
|---|---|---|---|---|
| $MEC1^{wt}$ (control) | 1 | — | — | 3 |
| $MEC1^{GAB1-less}$ | 0.22 | 0.01 | 0.14 | 3 |

For in vivo studies, the $50 \times 10^6$ of $MEC1^{wt}$ and $50 \times 10^6$ of $MEC1^{GAB1-less}$ cells (preparation of this cell line is described in the previous section) were separately stained either with CFSE or FarRed CellTrace dye (Thermo Fisher Scientific) according to manufacturer protocol. Stained cells were incubated overnight in normal media without Cell Trace dye (see Material and Method section). Next day, equal numbers of CFSE and FarRed stained cells (each $50 \times 10^6$) were mixed to obtain a mixed population with 1:1 ratio (validated by flow cytometry) and the total amount of $100 \times 10^6$ cells was subsequently resuspended in 100 μl of Phosphate buffer saline (PBS, catalog number: 5493; Sigma Aldrich) and injected into NSG mouse (Stock No:005557; The Jackson Laboratory) via the tail vein. Mice were sacrificed after 6 hours and analyzed for the presence of stained cells in different organs. All measurements were performed on BD FACS Verse (BD Biosciences). The final results for competitive migration assay were calculated as described in the previous section.

Tab.1D Here, we performed a competitive homing assay of MEC1$^{wt}$ (control) and MEC1$^{GAB1-less}$ cells in vivo. This revealed that the population of MEC1$^{GAB1-less}$ Cells was significantly retained in peripheral blood and was relatively less able to migrate to the spleen of NSG mice in comparison to control cells. The infiltration of other organs by MEC1$^{wt}$ and MEC1$^{GAB1-less}$ was not significantly affected by GAB1 knock-down.

TABLE 1D

|  | Ratio of migrated cells | P value (sample compared to control) | SD (standard deviation) | Number of replicates |
|---|---|---|---|---|
| Migration of MEC1$^{wt}$ cells (control) | 1 | — | — | 9 |
| Relative retention of MEC1$^{GAB1-less}$ cells in blood | 1.50 | 0.02 | 0.38 | 9 |
| Relative migration of MEC1$^{GAB1-less}$ cells in spleen | 0.75 | 0.01 | 0.20 | 9 |
| Relative migration of MEC1$^{GAB1-less}$ cells in bone marrow | 0.99 | 0.97 | 0.48 | 9 |
| Relative migration of MEC1$^{GAB1-less}$ cells in liver | 0.95 | 0.6 | 0.24 | 9 |

To investigate the impact of GAB1 protein on F-actin polymerization, we stimulated MEC1 and MEC1$^{GAB1-less}$ cell lines (for details of MEC1$^{GAB1-less}$ cell line generation, see the previous section) by 50% conditioned media (preparation of conditioned media is described in Material and Method section) for 10 minutes. This stimulation was immediately followed by performing of protocol for staining with Phalloidin-iFluor488 reagent according to manufacturer protocol (catalog number: ab176753; Abcam). The visualization of F-actin was executed by fluorescent microscopy (EVOS fl Imaging System, Thermo Fisher Scientific). This revealed that GAB1 is required for B cell polarisation and F-actin polymerization.

Figure 1B:
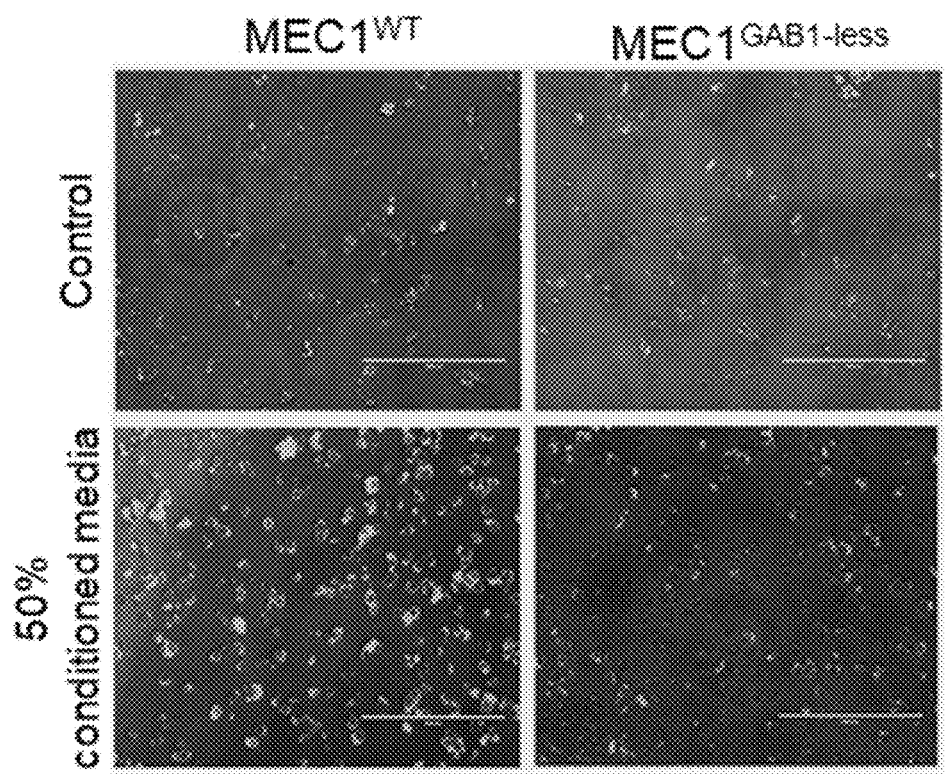
FIG. 1B shows the effect of chemokine-mediated (50% conditioned media) F-actin polymerization on control MEC1 cells (wild type, wt) and on MEC1$^{GAB1-less}$ cells (the generation of this cell line is described in the previous section).

FIG. 1B shows the effect of chemokine-mediated (50% conditioned media) F-actin polymerization on control MEC1 cells (wild type, wt) and on MEC1$^{GAB1-less}$ cells (the generation of this cell line is described in the previous section). The attenuation of GAB1 visibly decreases the F-actin polymerization (regions with brighter color).

Example 2—GAB1 Positively Modulates Tonic BCR Signaling and Inhibition of GAB1 Leads to Malignant B Cell Death MEC1 cells (2.5×10$^6$/ml) were transfected by NEON transfection system (catalog number: MPK10096; Thermo Fisher Scientific) in 100 μl reaction (program 1200 V/20 ms/2 pulses). The transfection buffer was supplemented with specific siRNA targeting GAB1 mRNA (ON-TARGETplus siRNA—Human; catalog number: L-003553-00-0005; Dharmacon) or nonspecific siRNA (ON-TARGETplus Non-targeting Pool; catalog number: D-001810-10-05; Dharmacon) to final concentration 1000 nM. Cells were incubated for 48 hours in IMDM media as described in the Material and Method section. After that, half of the cells from each variant were lysed and prepared for immunoblot (described in Material and Method section). The second half of each variant was activated by unlabeled goat F(ab')2 anti-human IgM (catalog number: 2022-01, Southern Biotech) by adding the required volume directly to the cell suspension to obtain final concentration 10 μg/ml of goat F(ab')2 anti-human IgM (anti-IgM). Cells were stimulated for 5 minutes and then lysed and prepared for immunoblot (described in the Material and Method section). To develop specific proteins we used these primary antibodies (concentration, catalog number, provider and origin): total-GAB1 (1:2000; #3232, Cell Signaling; rabbit); phospho-AKT Ser473 (1:2000; #4060, Cell Signaling; rabbit); total-AKT (1:3000; #2920, Cell Signaling; mouse); β-actin (1:5000; #4970, Cell Signaling; rabbit). Secondary antibodies were antibodies conjugated with horse-radish peroxidase (HRP) showing specificity against primary antibodies produced in mouse (1:3000; #7076, Cell Signaling) or rabbit (1:2000; #7074, Cell Signaling). The selection of the secondary antibody was dependent on the origin of the primary antibody.

Figure 2A:
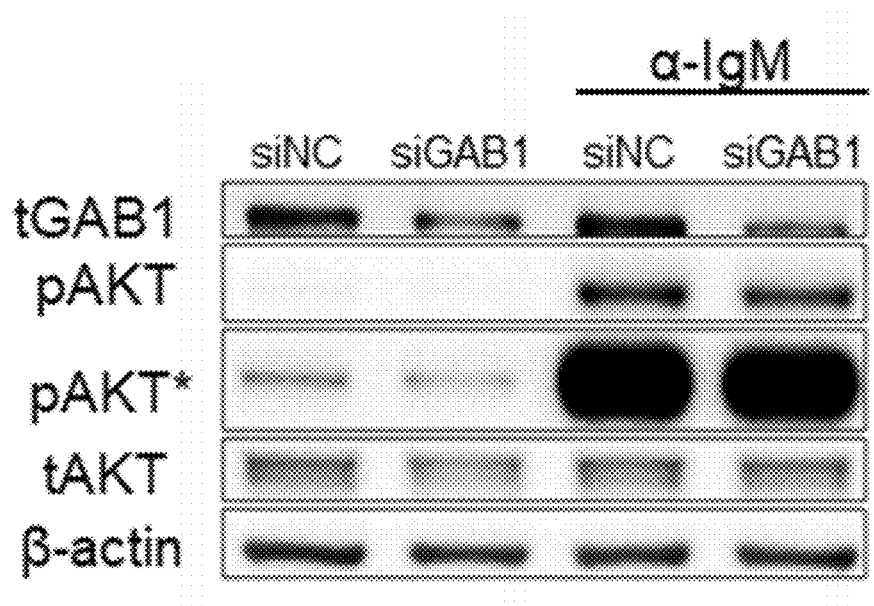
FIG. 2A shows that modulation of GAB1 levels by siRNA silencing affects not only the BCR-induced AKT activation but also the basal levels of AKT phosphorylation prior to BCR crosslinking.

FIG. 2A shows that modulation of GAB1 levels by siRNA silencing (siGAB1) in comparison to control cells (siNC) affects not only the BCR-induced AKT activation (anti-IgM), but also the basal levels of AKT phosphorylation prior to BCR crosslinking. Downregulation of GAB1 thus leads to inhibition of tonic AKT activity and BCR signaling.

Primary CLL cells (5×10$^6$/ml) were transfected by NEON transfection system (catalog number: MPK10096; Thermo Fisher Scientific) in 100 μl reaction (program 1200 V/20 ms/2 pulses). The transfection buffer was supplemented with specific siRNA targeting GAB1 mRNA (ON-TARGETplus siRNA—Human; catalog number: L-003553-00-0005; Dharmacon) or nonspecific siRNA (ON-TARGETplus Non-targeting Pool; catalog number: D-001810-10-05; Dharmacon) to final concentration 1000 nM. Cells were incubated for 48 hours in RPMI-1640 media as described in the Material and Method section. After that, the cells were lysed and prepared for immunoblot (described in the Material and Method section). To develop specific proteins we used these primary antibodies (concentration, catalog number, provider and origin): total-GAB1 (1:2000; #3232, Cell Signaling; rabbit); phospho-AKT Ser473 (1:2000; #4060, Cell Signaling; rabbit); total-AKT (1:3000; #2920, Cell Signaling; mouse); β-actin (1:5000; #4970, Cell Signaling; rabbit). Secondary antibodies were antibodies conjugated with horse-radish peroxidase (HRP) showing specificity against primary antibodies produced in mouse (1:3000; #7076, Cell Signaling) or rabbit (1:2000; #7074, Cell Signaling). The selection of the secondary antibody was dependent on the origin of the primary antibody.

Figure 2B:
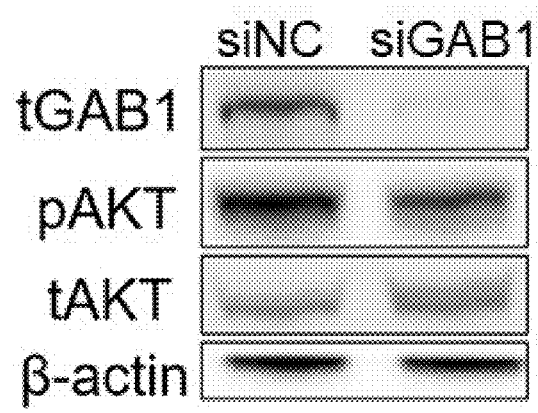
FIG. 2B shows that the silencing of GAB1 by specific siRNA leads to inhibition of AKT phosphorylation and thus inhibition of tonic signaling in primary CLL cells.

FIG. 2B shows that silencing of GAB1 by specific siRNA (siGAB1) leads to inhibition of AKT phosphorylation and thus inhibition of tonic signaling in primary CLL cells. Cells transfected with nonspecific siRNA were used as a control sample (siNC).

Figure 2C:
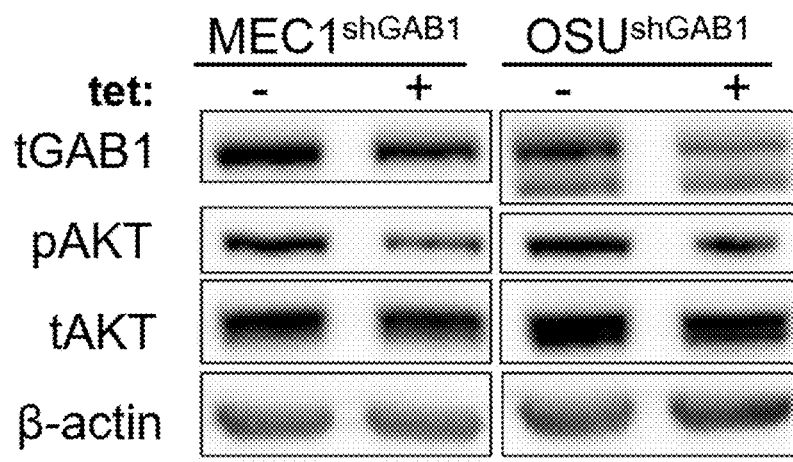
FIG. 2C shows another approach (shRNA expression) of GAB1 inhibition and its impact on tonic signaling inhibition.

The expression of shRNA targeting GAB1 mRNA in MEC1 cells or OSU-CLL cells (both derived from CLL) was performed using Tet-pLKO-puro plasmid (catalog number: #21915, Addgene). Specific sequence targeting GAB1 mRNA was designed according to instructions of plasmid provider (Tet-pLKO manual, catalog number: #21915 Addgene). Final sequence: 5'-CCGGAGT-TAACACACTCGTAGTATTCTCGAGAATAC-TACGAGTGTGTTAACTTTTTTG-3' (SEQ ID NO: 2) was purchased from Sigma Aldrich company and subsequently cloned into plasmid Tet-pLKO-puro according to instructions provided in Tet-pLKO manual. To produce viral particles containing DNA for tetracycline inducible shRNA against GAB1, 2 µg of Tet-pLKO-puro plasmid with cloned sequence was transfected into HEK293-FT cells together with 462 ng of pCMV-VSV-G (#8454, Addgene) and 3538 ng of dR8.91 (model: PVT2323, Life Science Market) plasmids. The cotransfection of these plasmids was performed by DharmaFECT Duo (Horizon Discovery) according to manufacturer protocol. Transfected HEK293-FT cells were subsequently cultivated as described in the Material and Method section for 48 hours. After that time, the cultivating media now containing viral particles was taken from HEK293-FT and was transferred to the desired B cell lines (MEC1 and OSU-CLL cells, both derived from CLL). B cell lines were subsequently cultivated in this virus-containing media for 24 hours. The next day were stably transduced cell lines selected by puromycin (3 µg/ml, Sigma Aldrich) for 5 days. After that were these selected cells cultivated as described in the Material and Method section for another two weeks in media without puromycin. After that time, expression of shRNA in different B cell lines was induced by adding tetracycline (1 µg/ml; Sigma Aldrich) into media (tet+) for 48 hours, and control cells were treated with vehicle (DMSO, tet-). Samples were subsequently lysed and prepared for immunoblot (see Material and Method section). To develop specific proteins we used these primary antibodies (concentration, catalog number, provider and origin): total-GAB1 (1:2000; #3232, Cell Signaling; rabbit); phospho-AKT Ser473 (1:2000; #4060, Cell Signaling; rabbit); total-AKT (1:3000; #2920, Cell Signaling; mouse); β-actin (1:5000; #4970, Cell Signaling; rabbit). Secondary antibodies were antibodies conjugated with horse-radish peroxidase (HRP) showing specificity against primary antibodies produced in mouse (1:3000; #7076, Cell Signaling) or rabbit (1:2000; #7074, Cell Signaling). The selection of secondary antibody was dependent on the origin of the primary antibody FIG. 2C shows another approach of GAB1 inhibition and its impact on inhibiting tonic signaling. Here, the universal effect of GAB1 on AKT activation was validated on 2 CLL-derived cell lines transduced with tetracycline-inducible shRNA against GAB1 (MEC1$^{shGAB1}$ and OSU-CLL$^{shGAB1}$). The induction of shRNA expression was performed by adding tetracycline (tet+) and control cells were treated with an equal volume of vehicle (DMSO, tet-).

In a further experiment, the 2.5×10$^6$/ml of MEC1 cells were transfected with the 2 µg of GAB1$^{MYC}$ plasmid (A. Yart et al. J Biol Chem. 2001; 276(12): 8856-64.) or by 2 µg of an empty control plasmid (#52535, Addgene). The cells were electroporated in 100 µl reaction by NEON electroporation system (program 1200 V/20 ms/2 pulses; catalog number: MPK10096; Thermo Fisher Scientific) according to manufacturer protocol. Cells were subsequently incubated for 48 hours as described in the Material and Method section. After that time cells were lysed and analyzed by immunoblot (described in the Material and Method section). To develop specific proteins we used these primary antibodies (concentration, catalog number, provider and origin): total-GAB1 (1:2000; #3232, Cell Signaling; rabbit); phospho-AKT Ser473 (1:2000; #4060, Cell Signaling; rabbit); total-AKT (1:3000; #2920, Cell Signaling; mouse); β-actin (1:5000; #4970, Cell Signaling; rabbit). Secondary antibodies were antibodies conjugated with horse-radish peroxidase (HRP) showing specificity against primary antibodies produced in mouse (1:3000; #7076, Cell Signaling) or rabbit (1:2000; #7074, Cell Signaling). The selection of the secondary antibody was dependent on the origin of the primary antibody.

Figure 2D:
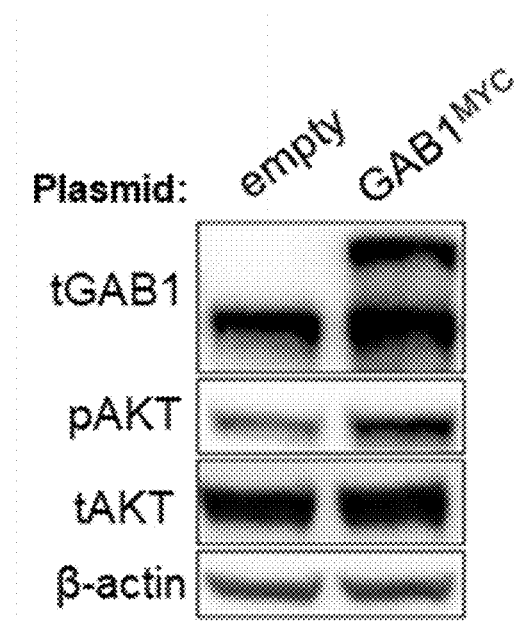
FIG. 2D shows that over-expression of GAB1 directly induces phosphorylation of AKT irrespectively of any ligation of surface receptors in B cells.

FIG. 2D To investigate whether the modulation of GAB1 protein level could affect the AKT activity without a direct role of BCR or other cell-surface receptor, we transfected the MEC1 cells with a plasmid for GAB1 over-expression. This revealed that over-expression of GAB1 directly induces phosphorylation of AKT irrespectively of ligation of cell-surface receptors in B cells. This proves a direct role of GAB1 protein in the regulation of tonic signaling in malignant cells.

Primary CLL cells (5×10$^6$/ml) was treated with 25 µM GAB1-001 inhibitor (inhGAB1-001) or 25 µM GAB1-004 inhibitor (inhGAB1-004) or by an equal volume of DMSO for 6 hours. These inhibitors were obtained from MD Anderson, USA (Lu Chen et al., PLoS Comput Biol. 2015; 11(1): e1004021.). After that, half the amount of each variant was immediately lysed and prepared for immunoblot (immunoblot is described in the Material and Method section). The second half of each variant was stimulated by goat F(ab')2 anti-human IgM (10 µg/mL; Southern Biotech) for 5 minutes and subsequently lysed and prepared for immunoblot (immunoblot is described in Material and Method section). To develop specific proteins we used these primary antibodies (concentration, catalog number, provider and origin): phospho-GAB1 Y627 (1:2000; #3233, Cell Signaling, rabbit); total-GAB1 (1:2000; #3232, Cell Signaling; rabbit); phospho-AKT Ser473 (1:2000; #4060, Cell Signaling; rabbit); total-AKT (1:3000; #2920, Cell Signaling; mouse); phospho-ERK Thr202/Tyr204 (1:3000; #4377, Cell Signaling; rabbit); total-ERK (1:3000; #4696, Cell Signaling; mouse); β-actin (1:5000; #4970, Cell Signaling; rabbit). Secondary antibodies were antibodies conjugated with horse-radish peroxidase (HRP) showing specificity against primary antibodies produced in mouse (1:3000; #7076, Cell Signaling) or rabbit (1:2000; #7074, Cell Signaling). The selection of secondary antibody was dependent on the origin of the primary antibody.

Figure 2E:
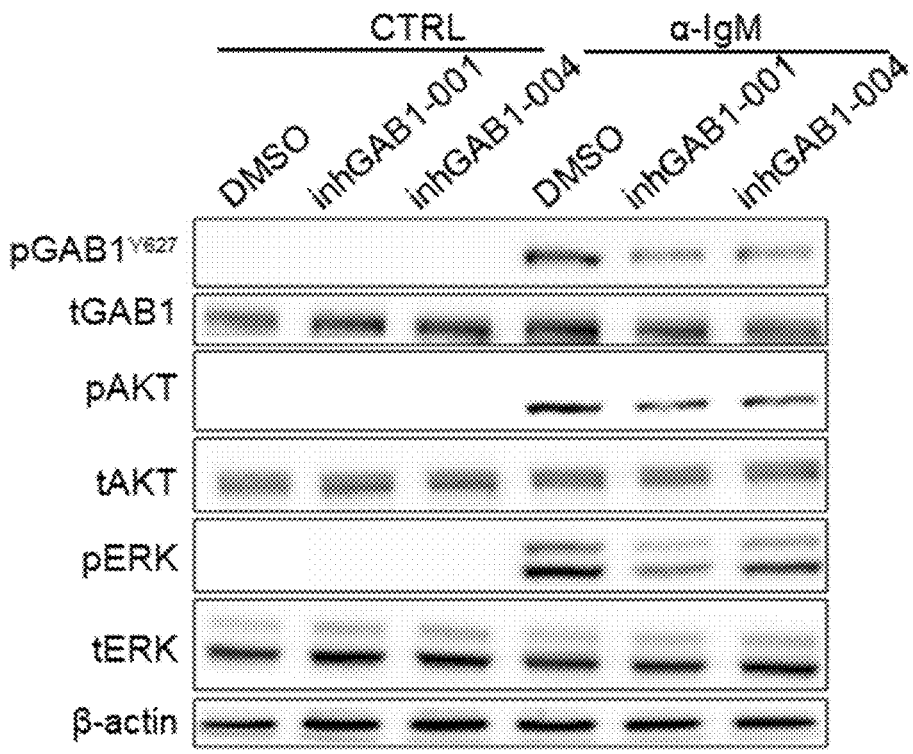
FIG. 2E shows that treatment of primary CLL cells with different types of GAB1 inhibitors leads to inhibition of GAB1 phosphorylation, inhibition of AKT and ERK phosphorylation after BCR crosslinking (α-IgM, also known as anti-IgM).

FIG. 2E shows that a treatment of primary CLL cells with different types of GAB1 inhibitors leads to inhibition of GAB1 phosphorylation, inhibition of AKT and ERK phosphorylation after BCR crosslinking (α-IgM, also known as anti-IgM).

Primary CLL cells (5×10$^6$/ml) were treated with different concentrations (10, 25 and 50 µM) of GAB1-001 inhibitor (inhGAB1-001) or GAB1-004 inhibitor (inhGAB1-004) for 6 hours (culture conditions are described in Material and Method section). These inhibitors were obtained from MD Anderson, USA (Lu Chen et al., PLoS Comput Biol. 2015; 11(1): e1004021.). Control cells were treated with an equal volume of DMSO or an equal volume of media (ctrl) also for 6 hours. After that, samples were immediately lysed and prepared for immunoblot (immunoblot is described in the Material and Method section). To develop specific proteins we used these primary antibodies (concentration, catalog number, provider and origin): phospho-GAB1 Y627 (1:2000; #3233, Cell Signaling, rabbit); total-GAB1 (1:2000; #3232, Cell Signaling; rabbit); phospho-AKT Ser473 (1:2000; #4060, Cell Signaling; rabbit); total-AKT (1:3000; #2920, Cell Signaling; mouse); phospho-ERK Thr202/Tyr204 (1:3000; #4377, Cell Signaling; rabbit); total-ERK (1:3000; #4696, Cell Signaling; mouse); β-actin (1:5000; #4970, Cell Signaling; rabbit). Secondary antibodies were antibodies conjugated with horse-radish peroxidase (HRP) showing specificity against primary antibodies produced in mouse (1:3000; #7076, Cell Signaling) or rabbit (1:2000; #7074, Cell Signaling). The selection of secondary antibody was dependent on the origin of the primary antibody.

Figure 2F:
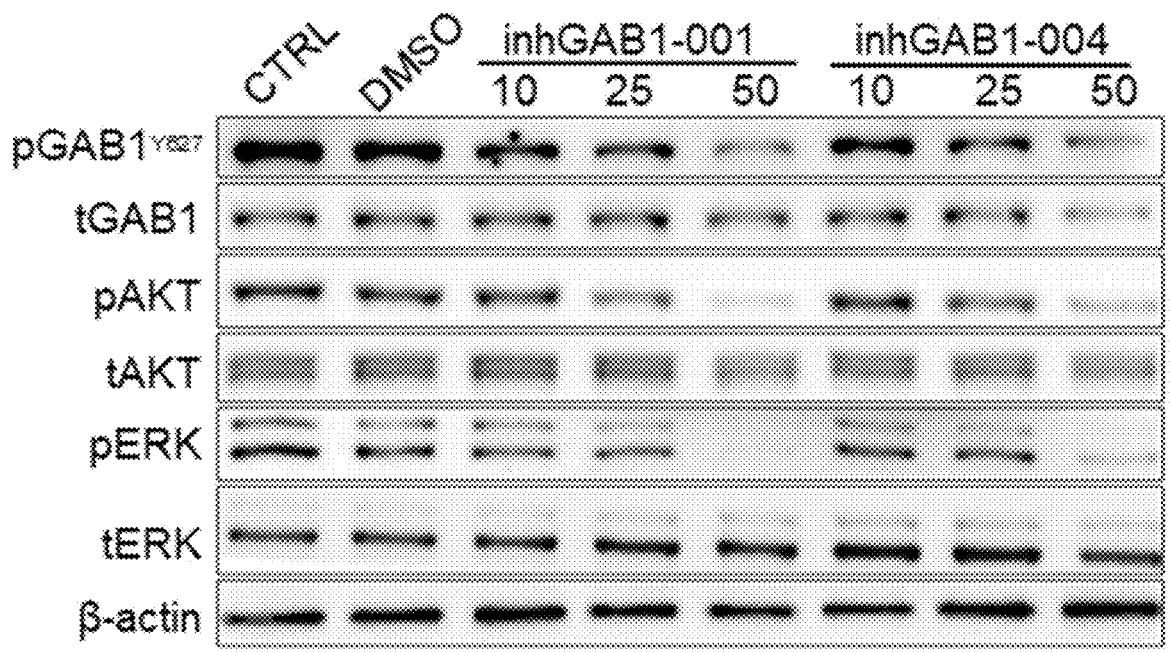
FIG. 2F shows that the treatment of primary CLL cells with GAB1 inhibitors leads to dose-dependent inhibition of basal GAB1 phosphorylation as well as inhibition of basal AKT and ERK phosphorylation. These data show that GAB1 inhibitors are potent to inhibit tonic signaling represented by phosphorylation of AKT.

FIG. 2F shows that the treatment of primary CLL cells with GAB1 inhibitors leads to dose-dependent inhibition of basal GAB1 phosphorylation as well as inhibition of basal AKT and ERK phosphorylation. These data show that GAB1 inhibitors are potent to inhibit tonic signaling represented by phosphorylation of AKT.

Primary CLL cells ($5 \times 10^6$/ml) were treated with 25 μM GAB1-001 inhibitor (inhGAB1-001) or GAB1-004 inhibitor (inhGAB1-004) for 6 hours (culture conditions are described in the Material and Method section). These inhibitors were obtained from MD Anderson, USA (Lu Chen et al., PLoS Comput Biol. 2015; 11(1): e1004021.). Control cells were treated with an equal volume of DMSO also for 6 hours. After that were these cells incubated in Hanks Balanced Salt Solution (HBSS, catalog number: H6648, Sigma Aldrich) containing 2 mM Fluo-4AM (catalog number: F14201, Thermo Fisher Scientific) for 30 minutes at 37° C. in the dark. The cells were subsequently prepared for analysis according to instructions provided by the manufacturer of Fluo-4AM. The malignant B cells were subsequently analyzed by flow cytometry (BD FACS Verse, BD Biosciences). Samples were acquired for 60 seconds without stimulation. After that the cells were immediately stimulated by SDF1 100 μg/ml (catalog number: 300-28A, Peprotech). Ionomycin (catalog number: 124222; Thermo Fisher Scientific) was added as a positive control according to manufacturer protocol. To calculate the response to SDF1, we established a baseline fluorescence threshold for each sample (by acquiring samples for 60 seconds without any stimulus). We then calculated the peak Fluo-4AM signal and the percentage of cells with fluorescence intensity above baseline Fluo-4AM signal following stimulation addition.

Figure 2G:
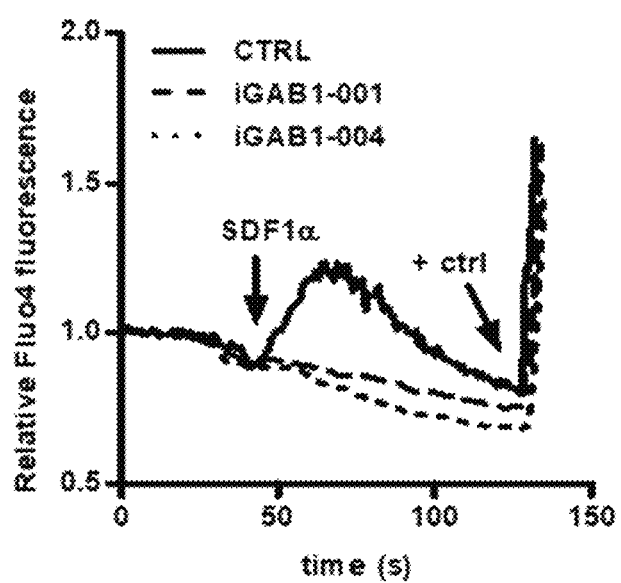
FIG. 2G shows that the treatment of primary CLL cells with GAB1 inhibitors decreases the Ca$^{2+}$ flux after treatment with SDF1.

FIG. 2G shows that the treatment of primary CLL cells with 25 μM GAB1-001 inhibitor (inhGAB1-001) or GAB1-004 inhibitor (inhGAB1-004) decreases the $Ca^{2+}$ flux after treatment with microenvironmental cytokines like SDF1, which is known for its involvement in the induction of cell migration.

To see the effect of GAB1 inhibitors on malignant B cell viability we treated $5 \times 10^6$/ml of primary CLL cells with different doses (10, 25 or 50 μM) of GAB1-001 inhibitor (inhGAB1-001) or GAB1-004 inhibitor (inhGAB1-004) for 48 hours. These inhibitors were obtained from MD Anderson, USA (Lu Chen et al., PLoS Comput Biol. 2015; 11(1): e1004021.). Control cells were treated with an equal volume of DMSO also for 48 hours (culture conditions are described in the Material and Method section). After that, the cells were stained with DiOC6/PI (3,3'-dihexyloxacarbocyanine iodide together with propidium iodide; catalog numbers: D273 and P3566; both were obtained from Thermo Fisher Scientific). Cells were stained and analyzed according to manufacturer protocol. The analysis was performed using BD FACS Verse flow cytometer (BD Biosciences).

Tab. 2A shows that the treatment with GAB1 inhibitors leads to dose-dependent decrease in viability of primary CLL cells. Altogether, these data prove that inhibition of GAB1 with inhibitors affects tonic signaling (represented by basal AKT phosphorylation) and the viability of malignant B cells.

TABLE 2A

|  | % of viability | P value (sample compared to control) | SD (standard deviation) | Number of replicates |
|---|---|---|---|---|
| DMSO (control) | 55.67 | — | 6.94 | 5 |
| 10 μM inhGAB1-001 | 52.83 | 0.3 | 9.7 | 5 |
| 25 μM inhGAB1-001 | 50.32 | 0.05 | 7.22 | 5 |
| 50 μM inhGAB1-001 | 30.98 | <0.001 | 6.42 | 5 |
| 10 μM inhGAB1-004 | 44.69 | 0.07 | 7.19 | 5 |
| 25 μM inhGAB1-004 | 42.59 | 0.1 | 10.20 | 5 |
| 50 μM inhGAB1-004 | 37.43 | 0.007 | 8.02 | 5 |

Example 3—Ibrutinib Treatment Leads to GAB1 Induction and Compensatory Activation of AKT in Malignant B Cells It is now well-recognized that the treatment of patients with ibrutinib, an inhibitor of BCR-associated kinase BTK, leads to transient lymphocytosis by interfering with BCR signaling, chemokine signaling, and B cell adhesion. Here we prove that inhibition of BTK by ibrutinib affects the GAB1 axis.

MEC1 cells ($2.5 \times 10^6$/ml) were treated with BTK inhibitor ibrutinib (PCI-32765; Selleckchem) at final concentration 1 μM. Control samples (−) were treated with equal volume of DMSO. Cells were subsequently cultivated for 2 hours, 1 day, 3 days or 5 days, as described in the Material and Method section. BTK inhibitor and DMSO were supplemented each second day. Cells were harvested at indicated time points and prepared for immunoblot analysis. immunoblot analysis and protein preparation are described in Material and Method section. To develop specific proteins we used these primary antibodies (concentration, catalog number, provider and origin): phospho-GAB1 Y307 (1:2000; #3234, Cell Signaling; rabbit); total-GAB1 (1:2000; #3232, Cell Signaling; rabbit); phospho-BTK Tyr223 (1:2000; #87457, Cell Signaling; rabbit); total-BTK (1:2000; #8547, Cell Signaling; rabbit); phospho-AKT Ser473 (1:2000; #4060, Cell Signaling; rabbit); total-AKT (1:3000; #2920, Cell Signaling; mouse); β-actin (1:5000; #4970, Cell Signaling; rabbit). Secondary antibodies were antibodies conjugated with horse-radish peroxidase (HRP) showing specificity against primary antibodies produced in mouse (1:3000; #7076, Cell Signaling) or rabbit (1:2000; #7074, Cell Signaling). The selection of secondary antibody was dependent on the origin of the primary antibody.

Figure 3A:
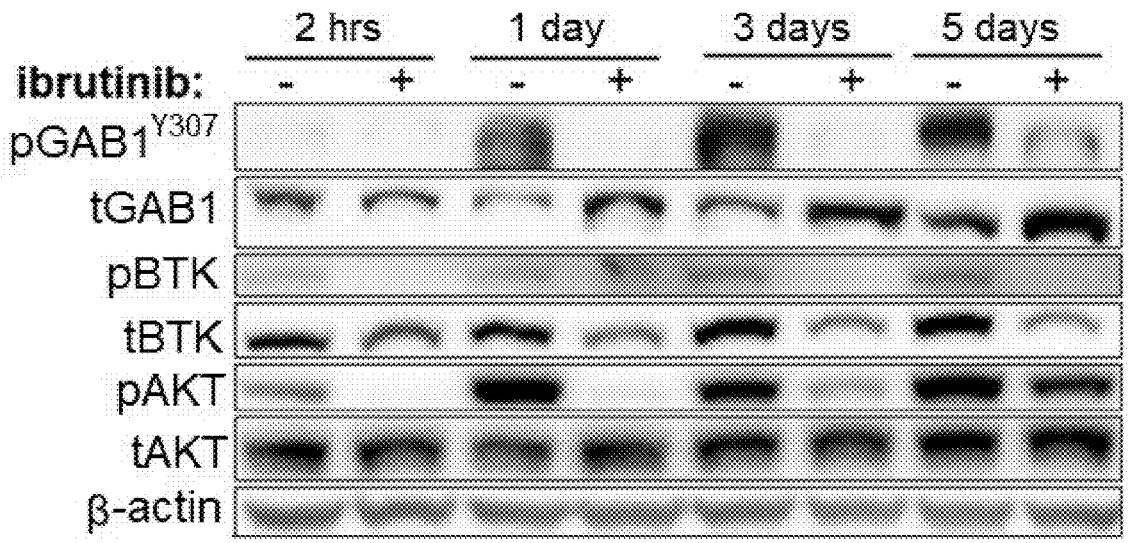
FIG. 3A shows that in vitro treatment of MEC1 cells with ibrutinib for prolonged periods of time leads to the accumulation of GAB1 proteins and restoration of basal AKT phosphorylation.

FIG. 3A shows that in vitro treatment of MEC1 cells with ibrutinib (ibrutinib+) for prolonged periods of time leads to the accumulation of GAB1 protein and restoration of basal AKT phosphorylation.

The samples from ibrutinib-treated patients were collected at a day before ibrutinib administration (PRE) and during therapy at the indicated time points (day 6 and week 8 in CLL_16; and day 3, week 4 and 15 in CLL_17). Patients were treated once daily with 420 mg of ibrutinib per os according to Summary of Product Characteristics (SPC) published by EMEA as valid on the day of filing of this application. Isolation of malignant B cells is described in Material and Method section. Samples were immediately harvested for immunoblot. immunoblot analysis and protein preparation are described in the Method section. To develop specific proteins we used these primary antibodies (concentration, catalog number, provider and origin): total-GAB1 (1:2000; #3232, Cell Signaling; rabbit); phospho-AKT Ser473 (1:2000; #4060, Cell Signaling; rabbit); total-AKT (1:3000; #2920, Cell Signaling; mouse); β-actin (1:5000; #4970, Cell Signaling; rabbit). Secondary antibodies were antibodies conjugated with horse-radish peroxidase (HRP) showing specificity against primary antibodies produced in mouse (1:3000; #7076, Cell Signaling) or rabbit (1:2000; #7074, Cell Signaling). The selection of secondary antibody was dependent on the origin of the primary antibody.

Figure 3B:
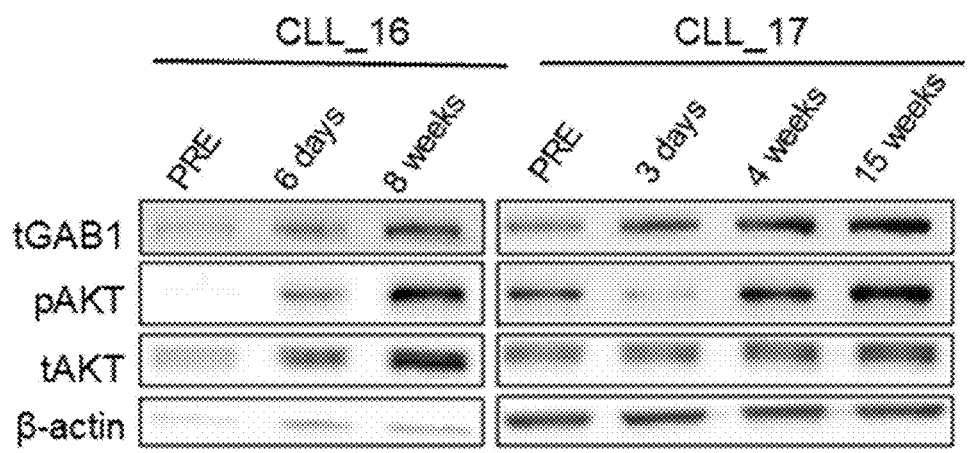
FIG. 3B shows that in vivo treatment of primary CLL cells with ibrutinib for prolonged periods of time leads to the accumulation of GAB1 proteins and restoration of basal AKT phosphorylation.

FIG. 3B shows that in vivo treatment of CLL patients with ibrutinib for prolonged periods of time leads to the accumulation of GAB1 protein and restoration of basal AKT phosphorylation in malignant B cells.

The samples from ibrutinib-treated patients were collected on a day before ibrutinib administration and during the second week on therapy. Patients were treated once daily with 420 mg of ibrutinib per os according to Summary of Product Characteristics (SPC) published by EMEA as valid on the day of filing of this application. Isolation of malignant B cells is described in the Material and Method section. Samples were immediately harvested for immunoblot. immunoblot analysis and protein preparation are described in the Method section. The intensity of bands for total GAB1 and phospho-AKT were quantified by software provided by UVITEC Cambridge (Alliance 4.7) according to manufacturer instructions. Measured values from samples collected during ibrutinib therapy were normalized to values obtained from the control sample (before ibrutinib therapy).

Tab. 3A shows statistical analysis of normalized densitometric data for immunoblots of samples from CLL patients (n=11) before and during ibrutinib therapy (samples were collected during second week of therapy). This graph shows that treatment with ibrutinib leads to significant upregulation of GAB1 protein. Here we also show the strengthening of tonic BCR signaling represented by basal phosphorylation of AKT.

TABLE 3A

| Protein | Normalised density of proteins | P value (sample compared to control) | SD (standard deviation) | N (number of replicates) |
|---|---|---|---|---|
| Before therapy | 1 | — | — | 11 |
| AKT phosphorylation | 1.48 | 0.04 | 0.66 | 11 |
| Total GAB1 | 1.47 | 0.03 | 0.61 | 11 |

MEC1$^{wt}$ (2.5×10$^6$/ml) and of MEC$^{GAB1-less}$ (2.5×10$^6$/ml) cells (their generation is described in example 1) was treated with ibrutinib (PCI-32765; Selleckchem) at final concentration 1 μM, or with an equal volume of vehicle (DMSO) for 7 days. Ibrutinib and DMSO were supplemented each second day. Cells were cultured as described in the Material and Method section. After that, cells were harvested and prepared for immunoblot analysis. immunoblot analysis and protein preparation are described in Method section. To develop specific proteins we used these primary antibodies (concentration, catalog number, provider and origin): total-GAB1 (1:2000; #3232, Cell Signaling; rabbit); phospho-BTK Tyr233 (1:2000; #87457, Cell Signaling; rabbit); total-BTK (1:2000; #8547, Cell Signaling; rabbit); phospho-AKT Ser473 (1:2000; #4060, Cell Signaling; rabbit); total-AKT (1:3000; #2920, Cell Signaling; mouse); β-actin (1:5000; #4970, Cell Signaling; rabbit). Secondary antibodies were antibodies conjugated with horse-radish peroxidase (HRP) showing specificity against primary antibodies produced in mouse (1:3000; #7076, Cell Signaling) or rabbit (1:2000; #7074, Cell Signaling). The selection of secondary antibody was dependent on the origin of the primary antibody.

Figure 3C:
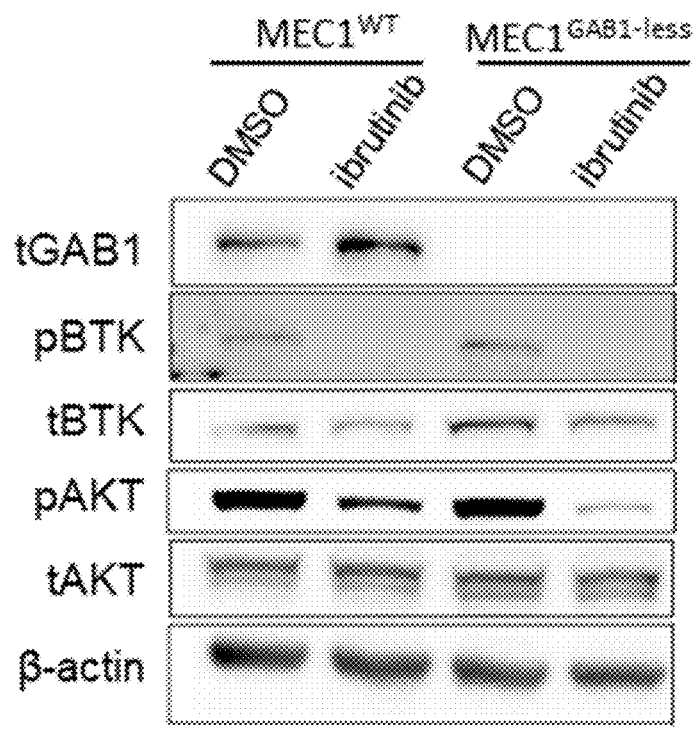
FIG. 3C shows the representative immunoblot of MEC1 and MEC1$^{GAB1-less}$ cells treated with ibrutinib (ibrutinib; 1 μM) or vehicle (DMSO) for 7 days.

FIG. 3C shows the representative immunoblot of MEC1$^{wt}$ and MEC1$^{GAB1-less}$ cells treated with ibrutinib or vehicle (DMSO) for 7 days. This demonstrates that the knock-down of GAB1 prevented the restoration of AKT phosphorylation in ibrutinib treated cells. This proves the direct role of GAB1 protein in the restoration of basal AKT activity in response to BTK inhibition.

Altogether this data suggests that GAB1 induced phosphorylation of AKT contributes to the adaptation of CLL cells to ibrutinib, and their extended survival. This stems from the mechanism described above where the basal levels of AKT phosphorylation are balanced by GAB1 axis.

MEC1 cells (2.5×10$^6$/ml) was treated with BTK inhibitor ibrutinib (PCI-32765; Selleckchem) at final concentration 1 μM or an equal volume of vehicle (DMSO). Ibrutinib and DMSO were supplemented each second day. After one day of treatment, one-quarter of the ibrutinib treated cells were harvested and prepared for immunoblot (see Material and Method section). The rest of the cells were cultivated for another six days (see Material and Method section). After that, the ibrutinib treated cells were treated with two different GAB1 inhibitors (inhGAB1-001 and inhGAB1-004; provided by MD Anderson, Lu Chen et al., PLoS Comput Biol. 2015; 11(1): e1004021.) at final concentration 25 μM, or with an equal volume of vehicle (DMSO) for another 24 hours. Cells were subsequently harvested and prepared for immunoblot analysis. immunoblot analysis and protein preparation are described in the Method section. To develop specific proteins we used these primary antibodies (concentration, catalog number, provider and origin): phospho-GAB1 Y627 (1:2000; #3233, Cell Signaling; rabbit); total-GAB1 (1:2000; #3232, Cell Signaling; rabbit); phospho-AKT Ser473 (1:2000; #4060, Cell Signaling; rabbit); total-AKT (1:3000; #2920, Cell Signaling; mouse); β-actin (1:5000; #4970, Cell Signaling; rabbit). Secondary antibodies were antibodies conjugated with horse-radish peroxidase (HRP) showing specificity against primary antibodies produced in mouse (1:3000; #7076, Cell Signaling) or rabbit (1:2000; #7074, Cell Signaling). The selection of secondary antibody was dependent on the origin of the primary antibody.

Figure 3D:
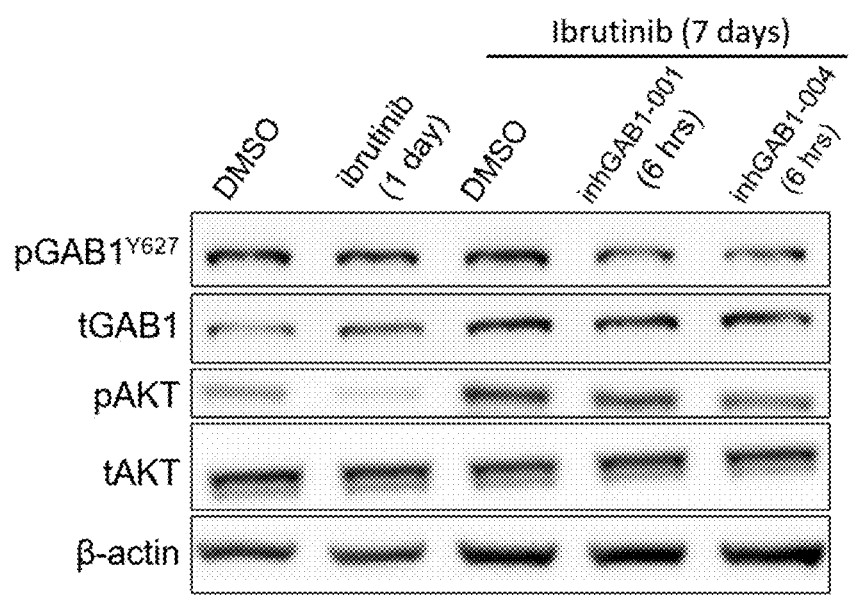
FIG. 3D shows that GAB1 inhibitor represses the AKT phosphorylation induced by prolonged exposure of MEC1 cells to ibrutinib.

FIG. 3D shows that GAB1 inhibitor represses the AKT phosphorylation induced by prolonged exposure of MEC1 cells to ibrutinib. This provides evidence that our novel strategy (inhibition of an adaptor protein, namely GAB1) in treatment of malignant B cells blocks the compensatory AKT activation.

MEC1 cells (2.5×10$^6$/ml) was treated with BTK inhibitor ibrutinib (PCI-32765; Selleckchem) at final concentration 1 μM or with equal volume of vehicle (DMSO). Cells were cultivated for six days (see Material and Method section) and ibrutinib or DMSO were supplemented each second day. After that DMSO (control cells) and ibrutinib treated cells were treated with two different GAB1 inhibitors (inhGAB1-001 and inhGAB1-004; provided by MD Anderson, Lu Chen et al., PLoS Comput Biol. 2015; 11(1): e1004021.) at final concentration 25 μM, or with an equal volume of vehicle (DMSO) for 48 hours. After that were cells harvested and stained for viability using DiOC6/PI (3,3'-dihexyloxacarbocyanine iodide together with propidium iodide (catalog numbers: D273 and P3566; both were obtained from Thermo Fisher Scientific). Cells were stained and analyzed according to manufacturer protocol. The analysis was performed using BD FACS Verse flow cytometer (BD Biosciences).

Tab. 3B shows that combinatory treatment with BTK inhibitor (ibrutinib) and GAB1 inhibitors (inhGAB1-001 and inhGAB1-004) act synergistically and contribute to increased apoptosis in MEC1 cells.

TABLE 3B

| Treatment | % of viability | P value (sample compared to control) | SD (standard deviation) | N (number of replicates) |
|---|---|---|---|---|
| DSMO (control) | 85.20 | — | — | 5 |
| BTK inhibitor (ibrutinib) | 81.66 | 0.02 | 6.23 | 5 |
| inhGAB1-001 | 67.00 | 0.01 | 2.71 | 5 |
| inhGAB1-004 | 74.52 | 0.05 | 5.21 | 5 |
| inhGAB1-001 plus BTK inhibitor (ibrutinib) | 58.64 | 0.001 | 4.01 | 5 |
| inhGAB1-004 plus BTK inhibitor (ibrutinib) | 66.55 | 0.01 | 7.78 | 5 |

Example 4—the Treatment of Other Types of Leukemias/Lymphomas with GAB1 Inhibitor Alone or in Combination with BTK Inhibitor Significantly Affects the Viability of Malignant Cells Primary CLL cells ($5 \times 10^6$/ml) were treated with two different GAB1 inhibitors (inhGAB1-001 and inhGAB1-004; provided by MD Anderson, US (Lu Chen et al., PLoS Comput Biol. 2015; 11(1): e1004021.) at final concentration 50 µM, or an equal volume of vehicle (DMSO). All variants were additionally treated with ibrutinib (PCI-32765; Selleckchem) at the final concentration 1 µM or an equal volume of vehicle (DMSO). Cells were incubated for 12 hours as described in the Material and Method section. After that, treated cells were stained with CFSE (Thermo Fisher Scientific, catalog number: C34554) or with FarRed (Thermo Fisher Scientific, catalog number: C34564) CellTrace dye. To compare the migration, the stained cells (control cells plus one treated variant) were mixed in ratio 1:1 and loaded in transwell inserts (24 well insert, 8 µm pore size; Falcon, Corning) according to manufacturer protocol. The migration towards conditioned media (diluted to final concentration of 50%; preparation of conditioned media is described in Material and Method section) was allowed for 6 hours and subsequently, the ratio of migrated (cells migrated through the transwell) CFSE or FarRed positive cells was detected by flow cytometry (BD FACS Verse, BD Biosciences). To detect the signal by flow cytometry, we followed the instructions provided by the manufacturer of these dyes (Thermo Fisher Scientific). The percentage of control cells was set to 1. The ratio of migrated inhibitor-treated cells was calculated by dividing of the percentage of migrated inhibitor-treated cells by percentage of migrated control cells.

Tab. 4A shows a result for the migration capacity (competitive migration assay) of primary CLL cells after treatment with either one of the two different GAB1 inhibitors or BTK inhibitor or their combinations. These data show, that inhibition of GAB1 protein by specific GAB1 inhibitors significantly reduces the migration potential of malignant B cells towards soluble factors produced by supportive cells.

TABLE 4A

| Treatment | Ratio of migrated cells | P value (sample compared to control) | SD (standard deviation) | N (number of replicates) |
|---|---|---|---|---|
| DSMO (control) | 1 | — | — | 7 |
| BTK inhibitor (ibrutinib) | 0.71 | 0.002 | 0.14 | 7 |
| inhGAB1-001 | 0.79 | 0.02 | 0.16 | 7 |
| inhGAB1-001 plus BTK inhibitor (ibrutinib) | 0.79 | 0.003 | 0.072 | 7 |
| inhGAB1-004 | 0.75 | 0.0002 | 0.082 | 7 |
| inhGAB1-004 plus BTK inhibitor (ibrutinib) | 0.68 | 0.0007 | 0.13 | 7 |

In a further experiment, $2.5 \times 10^6$/ml of JEKO (derived from mantle cell lymphoma) or ML2 (derived from acute myeloid leukemia) or OciLy5 (derived from small lymphocytic lymphoma) cells was treated with BTK inhibitor ibrutinib (PCI-32765; Selleckchem) at final concentration 1 µM or with an equal volume of vehicle (DMSO). Cells were cultivated for six days (see Material and Method section) and ibrutinib or DMSO were supplemented each second day. After that, DMSO (control cells) or ibrutinib treated cells were treated with two different GAB1 inhibitors (inhGAB1-001 and inhGAB1-004; provided by MD Anderson, USA (Lu Chen et al., PLoS Comput Biol. 2015; 11(1): e1004021.) at final concentration 25 µM, or with an equal volume of vehicle (DMSO) for another 48 hours. After that, cells were harvested and stained for viability using DiOC6/PI (3,3'-dihexyloxacarbocyanine iodide together with propidium iodide; catalog numbers: D273 and P3566; both were obtained from Thermo Fisher Scientific). Cells were stained and analyzed according to manufacturer protocol. The analysis was performed using BD FACS Verse flow cytometer (BD Biosciences).

Tab. 4B shows that treatment of different malignant B cells (derived from mantle cell lymphoma, acute myeloid leukemia, small lymphocytic lymphoma) with GAB1 inhibitor alone leads to significant induction of apoptosis. This figure also shows that combinatory treatment with GAB1 inhibitor and BTK inhibitor (ibrutinib) exhibit a synergistic effect and decreases the viability of malignant cells.

TABLE 4B

| Cell type | Treatment | % of viability | P value (sample compared to control) | SD (standard deviation) | N (number of replicates) |
|---|---|---|---|---|---|
| JEKO (Mantle cell lymphoma) | DSMO (control) | 76.64 | — | 0.96 | 3 |
| | BTK inhibitor (ibrutinib) | 60.14 | <0.001 | 1.16 | 3 |
| | inhGAB1-001 | 2.88 | <0.001 | 0.35 | 3 |
| | inhGAB1-004 | 49.20 | <0.001 | 0.79 | 3 |

TABLE 4B-continued

| Cell type | Treatment | % of viability | P value (sample compared to control) | SD (standard deviation) | N (number of replicates) |
|---|---|---|---|---|---|
| | inhGAB1-001 plus BTK inhibitor (ibrutinib) | 2.71 | <0.001 | 0.39 | 3 |
| | inhGAB1-004 inhibitor plus BTK inhibitor (ibrutinib) | 7.91 | <0.001 | 0.49 | 3 |
| ML2 (Acute myeloid leukemia) | DSMO (control) | 76.92 | — | 1.15 | 3 |
| | BTK inhibitor (ibrutinib) | 68.93 | 0.05 | 2.21 | 3 |
| | inhGAB1-001 | 6.86 | <0.001 | 0.23 | 3 |
| | inhGAB1-004 | 28.07 | 0.002 | 2.92 | 3 |
| | inhGAB1-001 plus BTK inhibitor (ibrutinib) | 2.13 | <0.001 | 0.37 | 3 |
| | inhGAB1-004 inhibitor plus BTK inhibitor (ibrutinib) | 13.70 | 0.001 | 2.40 | 3 |
| OciLy5 (Small lymphocytic leukemia) | DSMO (control) | 81.47 | — | 9.89 | 3 |
| | BTK inhibitor (ibrutinib) | 80.33 | 0.9 | 0.86 | 3 |
| | inhGAB1-001 | 53.12 | 0.05 | 2.78 | 3 |
| | inhGAB1-004 | 62.46 | 0.059 | 1.60 | 3 |
| | inhGAB1-001 plus BTK inhibitor (ibrutinib) | 45.97 | 0.03 | 1.11 | 3 |
| | inhGAB1-004 inhibitor plus BTK inhibitor (ibrutinib) | 49.81 | 0.04 | 1.74 | 3 |

In a further experiment, $2.5 \times 10^6$/ml of RAMOS (derived from Burkitt's lymphoma) or DOHH2 (derived from diffuse large B cell lymphoma) or GRANTA (derived from acute lymphoblastic leukemia) or WSU-NHL (derived from follicular lymphoma) cells was treated with treated with two different GAB inhibitors (inhGAB1-001 and inhGAB1-004; provided by MD Anderson, USA (Lu Chen et al., PLoS Comput Biol. 2015; 11(1): e1004021.) at final concentration 25 µM, or with an equal volume of vehicle (DMSO) for 48 hours. After that, cells were harvested and stained for viability using DiOC6/PI (3,3'-dihexyloxacarbocyanine iodide together with propidium iodide; catalog numbers: D273 and P3566; both were obtained from Thermo Fisher Scientific). Cells were stained and analyzed according to manufacturer protocol. The analysis was performed using BD FACS Verse flow cytometer (BD Biosciences).

Tab. 4C shows that treatment of different B cell malignancies (derived from Burkitt's lymphoma, diffuse large B cell lymphoma, acute lymphoblastic leukemia, or follicular lymphoma) with GAB1 inhibitor alone leads to significant induction of cell apoptosis.

TABLE 4C

| Cell type | Treatment | % of viability | P value (sample compared to control) | SD (standard deviation) | N (number of replicates) |
|---|---|---|---|---|---|
| RAMOS (Burkitt's lymphoma) | DSMO (control) | 95.01 | — | 1.61 | 3 |
| | inhGAB1-001 | 50.27 | <0.001 | 1.01 | 3 |
| | inhGAB1-004 | 74.64 | 0.01 | 2.92 | 3 |
| DOHH2 (GC-DLBCL) | DSMO (control) | 81.84 | — | 1.48 | 3 |
| | inhGAB1-001 | 51.91 | <0.001 | 1.56 | 3 |
| | inhGAB1-004 | 72.30 | 0.01 | 1.59 | 3 |
| GRANTA (Acute lymphoblastic leukemia) | DSMO (control) | 87.24 | — | 1.72 | 3 |
| | inhGAB1-001 | 4.49 | 0.004 | 1.30 | 3 |
| | inhGAB1-004 | 74.11 | 0.09 | 6.00 | 3 |
| WSU-NHL (Follicular lymphoma) | DSMO (control) | 87.34 | — | 2.31 | 3 |
| | inhGAB1-001 | 29.40 | 0.001 | 1.48 | 3 |
| | inhGAB1-004 | 70.18 | 0.02 | 5.03 | 3 |

What is claimed is:

1. A method of treatment of a hematological malignancy, said method comprising the step of administering at least one GAB1 inhibitor to a subject in need of such treatment; wherein the GAB1 inhibitor is a compound of formula III:

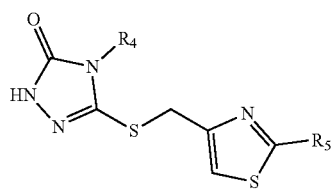

(III)

wherein
R5 is a benzene, or a (substituted) aryl group, or a (substituted) heteroaryl group; and
R4 is a moiety of formula IV:

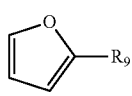

(IV)

wherein R9 is an alkyl bonded to the N group of formula III.

2. The method of claim 1, wherein the hematological malignancy is a myeloid neoplasm.

3. The method of claim 2, wherein the myeloid neoplasm is Myclodysplastic syndrome.

4. The method of claim 2, wherein the myeloid neoplasm is myeloid leukemia.

5. The method of claim 4, wherein the myeloid leukemia is Acute myeloid leukemia.

6. The method of claim 4, wherein the myeloid leukemia is Chronic myeloid leukemia.

7. The method of claim 4, wherein the myeloid leukemia is Monocytic leukemia.

8. The method of claim 4, wherein the myeloid leukemia is Promyelocytic leukemia.

9. The method of claim 1, wherein the hematological malignancy is a lymphoid neoplasm.

10. The method of claim 9, wherein the lymphoid neoplasm is Multiple myeloma.

11. The method of claim 9, wherein the lymphoid neoplasm is a lymphocytic leukemia.

12. The method of claim 11, wherein the lymphocytic leukemia is Chronic lymphocytic leukemia.

13. The method of claim 11, wherein the lymphocytic leukemia is Acute lymphocytic leukemia.

14. The method of claim 11, wherein the lymphocytic leukemia is Small lymphocytic leukemia.

15. The method of claim 9, wherein the lymphoid neoplasm is a lymphoma.

16. The method of claim 15, wherein the lymphoma is a relapsed or refractory lymphoma.

17. The method of claim 15, wherein the lymphoma is non-Hodgkin's lymphoma.

18. The method of claim 15, wherein the lymphoma is Mantle cell lymphoma.

19. The method of claim 15, wherein the lymphoma is Burkitt's lymphoma.

20. The method of claim 15, wherein the lymphoma is Diffuse large B cell lymphoma.

21. The method of claim 15, wherein the lymphoma is Follicular lymphoma.

22. The method of claim 15, wherein the lymphoma is Marginal zone lymphoma.

23. The method of claim 15, wherein the lymphoma is Hodgkin's lymphoma.

24. The method of claim 15, wherein the lymphoma is T cell lymphoma.

25. The method of claim 15, wherein the lymphoma is NK cell lymphoma.

26. The method of claim 15, wherein the lymphoma is Primary thyroid lymphoma.

27. The method of claim 15, wherein the lymphoma is Waldenstrom's macroglobulinemia.

28. A method of treatment of a hematological malignancy, said method comprising the step of administering at least one GAB1 inhibitor to a subject in need of such treatment; wherein the GAB1 inhibitor is a compound selected from the group consisting of:

inhGAB1-001

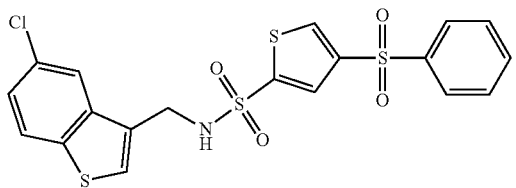

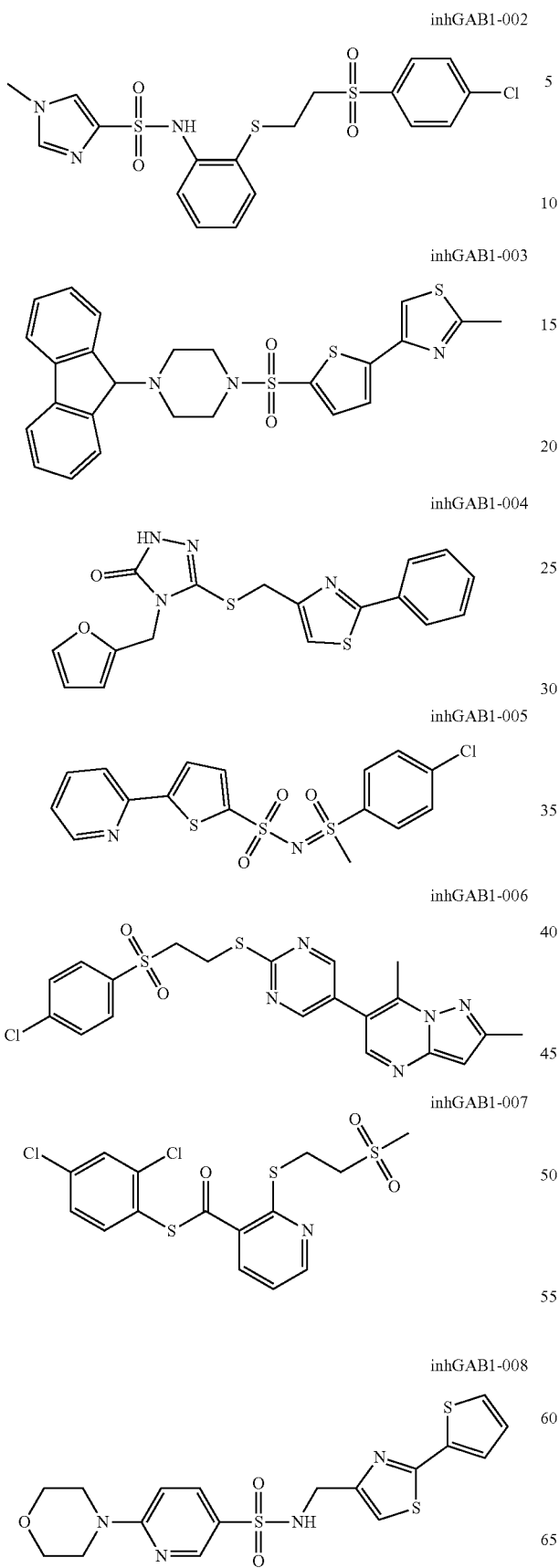
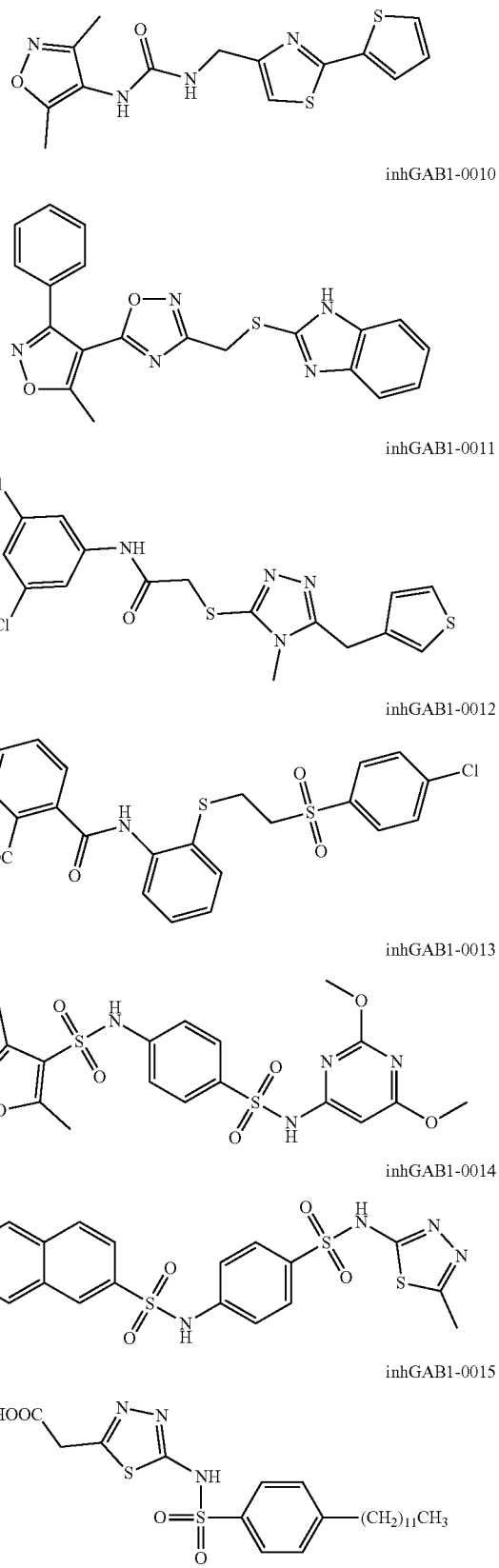

-continued inhGAB1-0016

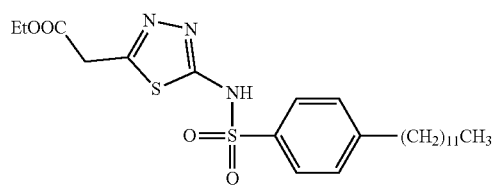

inhGAB1-0017

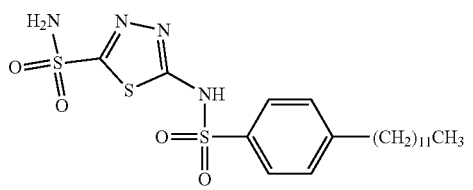

inhGAB1-0018

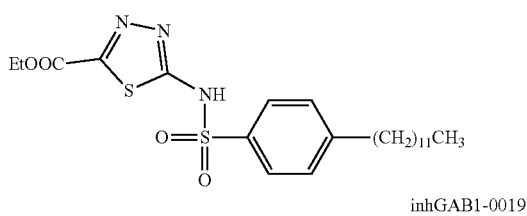

inhGAB1-0019

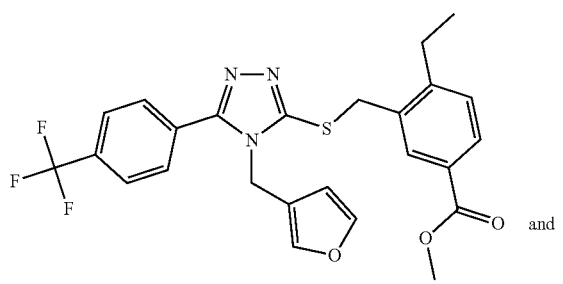

inhGAB1-0020

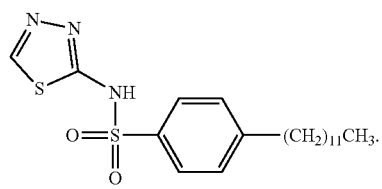

29. A method of treatment of at least one hematological malignancy, said method comprising a step of co-administering at least one GAB1 inhibitor and at least one BTK inhibitor;

wherein the GAB1 inhibitor is a compound of formula III:

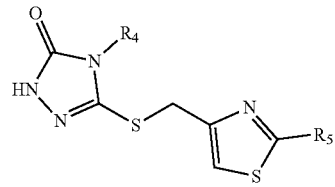

wherein

R5 is a benzene, or a (substituted) aryl group, or a (substituted) heteroaryl group; and R4 is a moiety of formula IV:

wherein R9 is an alkyl bonded to the N group.

30. The method of claim 29, wherein the step of co-administering at least one GAB1 inhibitor and at least one BTK inhibitor is a step of sequentially administering at least one GAB1 inhibitor and at least one BTK inhibitor.

31. The method of claim 29, wherein the step of co-administering at least one GAB1 inhibitor and at least one BTK inhibitor is a step of simultaneously administering at least one GAB1 inhibitor and at least one BTK inhibitor.

32. The method of claim 29, wherein the hematological malignancy is a myeloid neoplasm.

33. The method of claim 32, wherein the myeloid neoplasm is Myelodysplastic syndrome.

34. The method of claim 32, wherein the myeloid neoplasm is myeloid leukemia.

35. The method of claim 34, wherein the myeloid leukemia is Acute myeloid leukemia.

36. The method of claim 34, wherein the myeloid leukemia is Chronic myeloid leukemia.

37. The method of claim 34, wherein the myeloid leukemia is Monocytic leukemia.

38. The method of claim 34, wherein the myeloid leukemia is Promyelocytic leukemia.

39. The method of claim 29, wherein the hematological malignancy is a lymphoid neoplasm.

40. The method of claim 39, wherein the lymphoid neoplasm is Multiple myeloma.

41. The method of claim 39, wherein the lymphoid neoplasm is a lymphocytic leukemia.

42. The method of claim 41, wherein the lymphocytic leukemia is Chronic lymphocytic leukemia.

43. The method of claim 41, wherein the lymphocytic leukemia is Acute lymphocytic leukemia.

44. The method of claim 41, wherein the lymphocytic leukemia is Small lymphocytic leukemia.

45. The method of claim 39, wherein the lymphoid neoplasm is a lymphoma.

46. The method of claim 45, wherein the lymphoma is a relapsed or refractory lymphoma.

47. The method of claim 45, wherein the lymphoma is non-Hodgkin's lymphoma.

48. The method of claim 45, wherein the lymphoma is Mantle cell lymphoma.

49. The method of claim 45, wherein the lymphoma is Burkitt's lymphoma.

50. The method of claim 45, wherein the lymphoma is Diffuse large B cell lymphoma.

51. The method of claim 45, wherein the lymphoma is Folicular lymphoma.

52. The method of claim 45, wherein the lymphoma is Marginal zone lymphoma.

53. The method of claim 45, wherein the lymphoma is Hodgkin's lymphoma.

54. The method of claim 45, wherein the lymphoma is T cell lymphoma.

55. The method of claim 45, wherein the lymphoma is NK cell lymphoma.

56. The method of claim 45, wherein the lymphoma is Primary thyroid lymphoma.

57. The method of claim 45, wherein the lymphoma is Waldenstrom's macroglobulinemia.

58. A method of treatment of at least one hematological malignancy, said method comprising a step of co-administering at least one GAB1 inhibitor;

wherein the GAB1 inhibitor is a compound selected from the group consisting of:

inhGAB1-001

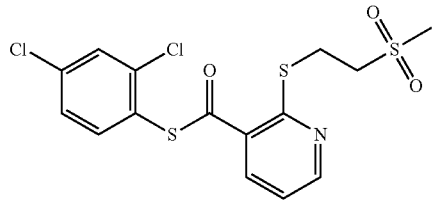

inhGAB1-002

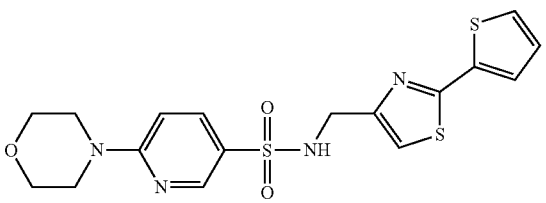

inhGAB1-003

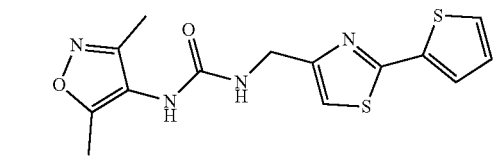

inhGAB1-004

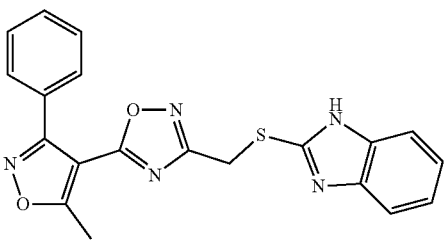

inhGAB1-005

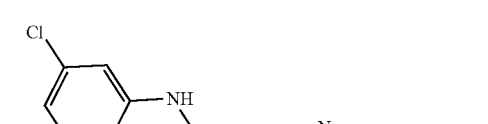

inhGAB1-006

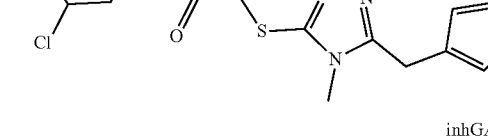

inhGAB1-007 inhGAB1-008 inhGAB1-009 inhGAB1-0010 inhGAB1-0011 inhGAB1-0012 inhGAB1-0013 and at least one BTK inhibitor.

59. The method according to claim 29, wherein the BTK inhibitor is selected from the group consisting of ibrutinib, acalabrutinib, zanubrutinib, GDC-0834; RN-486; CGI-560; CGI-1764; HM-71224; CC-292; ONO-4059; CNX-774; and LFM-A13.

60. The method of claim 28, wherein the hematological malignancy is a myeloid neoplasm.

61. The method of claim 60, wherein the myeloid neoplasm is Myelodysplastic syndrome.

62. The method of claim 60, wherein the myeloid neoplasm is myeloid leukemia.

63. The method of claim 62, wherein the myeloid leukemia is Acute myeloid leukemia.

64. The method of claim 62, wherein the myeloid leukemia is Chronic myeloid leukemia.

65. The method of claim 62, wherein the myeloid leukemia is Monocytic leukemia.

66. The method of claim 62, wherein the myeloid leukemia is Promyelocytic leukemia.

67. The method of claim 28, wherein the hematological malignancy is a lymphoid neoplasm.

68. The method of claim 67, wherein the lymphoid neoplasm is Multiple myeloma.

69. The method of claim 67, wherein the lymphoid neoplasm is a lymphocytic leukemia.

70. The method of claim 69, wherein the lymphocytic leukemia is Chronic lymphocytic leukemia.

71. The method of claim 69, wherein the lymphocytic leukemia is Acute lymphocytic leukemia.

72. The method of claim 69, wherein the lymphocytic leukemia is Small lymphocytic leukemia.

73. The method of claim 67, wherein the lymphoid neoplasm is a lymphoma.

74. The method of claim 73, wherein the lymphoma is a relapsed or refractory lymphoma.

75. The method of claim 73, wherein the lymphoma is non-Hodgkin's lymphoma.

76. The method of claim 73, wherein the lymphoma is Mande cell lymphoma.

77. The method of claim 73, wherein the lymphoma is Burkitt's lymphoma.

78. The method of claim 73, wherein the lymphoma is Diffuse large B cell lymphoma.

79. The method of claim 73, wherein the lymphoma is Follicular lymphoma.

80. The method of claim 73, wherein the lymphoma is Marginal zone lymphoma.

81. The method of claim 73, wherein the lymphoma is Hodgkin's lymphoma.

82. The method of claim 73, wherein the lymphoma is T cell lymphoma.

83. The method of claim 73, wherein the lymphoma is NK cell lymphoma.

84. The method of claim 73, wherein the lymphoma is Primary thyroid lymphoma.

85. The method of claim 73, wherein the lymphoma is Waldenstrom's macroglobulinemia.

86. The method of claim 58, wherein the step of co-administering the at least one GAB1 inhibitor and at least one BTK inhibitor is a step of sequentially administering the at least one GAB1 inhibitor and at least one BTK inhibitor.

87. The method of claim 58, wherein the step of co-administering the at least one GAB1 inhibitor and at least one BTK inhibitor is a step of simultaneously administering the at least one GAB1 inhibitor and at least one BTK inhibitor.

88. The method of claim 58, wherein the hematological malignancy is a myeloid neoplasm.

89. The method of claim 88, wherein the myeloid neoplasm is Myelodysplastic syndrome.

90. The method of claim 88, wherein the myeloid neoplasm is myeloid leukemia.

91. The method of claim 90, wherein the myeloid leukemia is Acute myeloid leukemia.

92. The method of claim 90, wherein the myeloid leukemia is Chronic myeloid leukemia.

93. The method of claim 90, wherein the myeloid leukemia is Monocytic leukemia.

94. The method of claim 90, wherein the myeloid leukemia is Promyelocytic leukemia.

95. The method of claim 58, wherein the hematological malignancy is a lymphoid neoplasm.

96. The method of claim 95, wherein the lymphoid neoplasm is Multiple myeloma.

97. The method of claim 95, wherein the lymphoid neoplasm is a lymphocytic leukemia.

98. The method of claim 97, wherein the lymphocytic leukemia is Chronic lymphocytic leukemia.

99. The method of claim 97, wherein the lymphocytic leukemia is Acute lymphocytic leukemia.

100. The method of claim 97, wherein the lymphocytic leukemia is Small lymphocytic leukemia.

101. The method of claim 95, wherein the lymphoid neoplasm is a lymphoma.

102. The method of claim 101, wherein the lymphoma is a relapsed or refractory lymphoma.

103. The method of claim 101, wherein the lymphoma is non-Hodgkin's lymphoma.

104. The method of claim 101, wherein the lymphoma is Mantle cell lymphoma.

105. The method of claim 101, wherein the lymphoma is Burkitt's lymphoma.

106. The method of claim 101, wherein the lymphoma is Diffuse large B cell lymphoma.

107. The method of claim 101, wherein the lymphoma is Folicular lymphoma.

108. The method of claim 101, wherein the lymphoma is Marginal zone lymphoma.

109. The method of claim 101, wherein the lymphoma is Hodgkin's lymphoma.

110. The method of claim 101, wherein the lymphoma is T cell lymphoma.

111. The method of claim 101, wherein the lymphoma is NK cell lymphoma.

112. The method of claim 101, wherein the lymphoma is Primary thyroid lymphoma.

113. The method of claim 101, wherein the lymphoma is Waldenstrom's macroglobulinemia.

114. The method according to claim 58, wherein the BTK inhibitor is selected from the group consisting of ibrutinib, acalabrutinib, zanubrutinib, GDC-0834; RN-486; CGI-560; CGI-1764; HM-71224; CC-292; ONO-4059; CNX-774; and LFM-A13.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: artificial
<220> FEATURE:
<223> OTHER INFORMATION: gRNA Example 1

```
<400> SEQUENCE: 1
ctacttggta gcagacagcg                                          20

<210> SEQ ID NO 2
<211> LENGTH: 58
<212> TYPE: DNA
<213> ORGANISM: artificial
<220> FEATURE:
<223> OTHER INFORMATION: shRNA targeting GAB1 mRNA, Example 2

<400> SEQUENCE: 2
ccggagttaa cacactcgta gtattctcga gaatactacg agtgtgttaa cttttttg     58
```